United States Patent
Lerner et al.

(10) Patent No.: US 9,661,992 B2
(45) Date of Patent: May 30, 2017

(54) METHOD AND APPARATUS FOR EXTENDING A TUBE

(71) Applicant: TORUS MEDICAL LTD., Beer Sheva (IL)

(72) Inventors: Vlad Lerner, Rehovot (IL); Levy Ulanovsky, Jerusalem (IL); Boris Levin, Rehovot (IL)

(73) Assignee: TORUS MEDICAL LTD., Beer Sheva (IL)

( * ) Notice: Subject to any disclaimer, the term of this patent is extended or adjusted under 35 U.S.C. 154(b) by 757 days.

(21) Appl. No.: 13/856,695

(22) Filed: Apr. 4, 2013

(65) Prior Publication Data

US 2013/0289350 A1    Oct. 31, 2013

Related U.S. Application Data

(63) Continuation-in-part of application No. 13/695,033, filed as application No. PCT/IL2010/000706 on Aug. 29, 2010.

(60) Provisional application No. 61/328,656, filed on Apr. 28, 2010.

(51) Int. Cl.
| | |
|---|---|
| *A61B 1/04* | (2006.01) |
| *A61B 1/00* | (2006.01) |
| *A61B 1/005* | (2006.01) |
| *A61B 1/015* | (2006.01) |
| *A61M 3/02* | (2006.01) |
| *A61M 25/01* | (2006.01) |

(52) U.S. Cl.
CPC .......... *A61B 1/005* (2013.01); *A61B 1/00151* (2013.01); *A61B 1/015* (2013.01); *A61M 3/0279* (2013.01); *A61M 3/0241* (2013.01); *A61M 3/0283* (2013.01); *A61M 3/0295* (2013.01); *A61M 25/0119* (2013.01)

(58) Field of Classification Search
CPC .... A61B 1/00133; A61B 1/00151; A61B 1/31
USPC ....... 600/109, 114, 116, 127, 139, 144, 155, 600/156; 604/101.01, 101.02, 101.03, 604/103.05, 104
See application file for complete search history.

(56) References Cited

U.S. PATENT DOCUMENTS

| | | |
|---|---|---|
| 3,881,485 A | 5/1975 | Davis, Jr. |
| 4,067,335 A | 1/1978 | Silvanov |
| 4,182,332 A | 1/1980 | Delaney |
| 4,403,982 A | 9/1983 | Clayton |
| 4,406,655 A | 9/1983 | Clayton |

(Continued)

*Primary Examiner* — Timothy J Neal
(74) *Attorney, Agent, or Firm* — Nixon & Vanderhye P.C.

(57) ABSTRACT

Apparatus and methods for extending a tube, the apparatus including a foldable tube having a folded portion inside an unfolded portion of the tube, and a source of fluid coupled to the unfolded portion for providing fluid into the unfolded portion to unfold and extend the folded portion out of the unfolded portion to become an extension of the unfolded portion. The apparatus and methods are useful, inter alia, for cleansing the colon in the normal direction, that is, from the cecum to the anus, using an apparatus that is introduced via the anus. A washing liquid is supplied deep into the colon via the soft feed tube that is inserted via the anus and is extended into the colon by inflation. The washing liquid is then drained out via the anus through a drainage channel.

28 Claims, 17 Drawing Sheets

(56) References Cited

U.S. PATENT DOCUMENTS

| | | | |
|---|---|---|---|
| 4,493,711 A * | 1/1985 | Chin | A61M 25/104 604/271 |
| 4,601,713 A * | 7/1986 | Fuqua | A61M 25/0023 604/103.14 |
| 4,842,583 A | 6/1989 | Majlessi | |
| 4,874,363 A | 10/1989 | Abell | |
| 5,019,056 A | 5/1991 | Lee et al. | |
| 5,049,138 A | 9/1991 | Chevalier et al. | |
| 5,176,630 A | 1/1993 | Shilling et al. | |
| 5,190,519 A | 3/1993 | Mead et al. | |
| 5,236,423 A * | 8/1993 | Mix | A61B 1/00151 600/115 |
| 5,322,070 A | 6/1994 | Goodman et al. | |
| 5,405,319 A | 4/1995 | Abell et al. | |
| 5,673,147 A | 9/1997 | McKinley | |
| 5,741,239 A | 4/1998 | Mulholland | |
| 5,751,341 A | 5/1998 | Chaleki et al. | |
| 5,941,860 A | 8/1999 | Wheeler | |
| 6,364,852 B1 * | 4/2002 | Lee | A61F 5/0093 604/12 |
| 6,503,195 B1 | 1/2003 | Keller et al. | |
| 6,563,105 B2 | 5/2003 | Seibel et al. | |
| 6,749,346 B1 | 6/2004 | Dickensheets et al. | |
| 6,798,570 B1 | 9/2004 | Greenberg | |
| 6,949,069 B2 | 9/2005 | Farkas et al. | |
| 6,984,226 B1 | 1/2006 | Abell et al. | |
| 6,988,988 B2 | 1/2006 | Voloshin et al. | |
| 7,364,588 B2 | 4/2008 | Mathis et al. | |
| 2001/0044595 A1 * | 11/2001 | Reydel | A61F 2/95 604/98.02 |
| 2002/0016607 A1 * | 2/2002 | Bonadio | A61B 17/3423 606/192 |
| 2003/0168068 A1 * | 9/2003 | Poole | A61B 1/00082 128/850 |
| 2007/0015965 A1 | 1/2007 | Cox et al. | |

\* cited by examiner

Fig. 2E-1   Fig. 2E-2   Fig. 2E-3   Fig. 2E-4

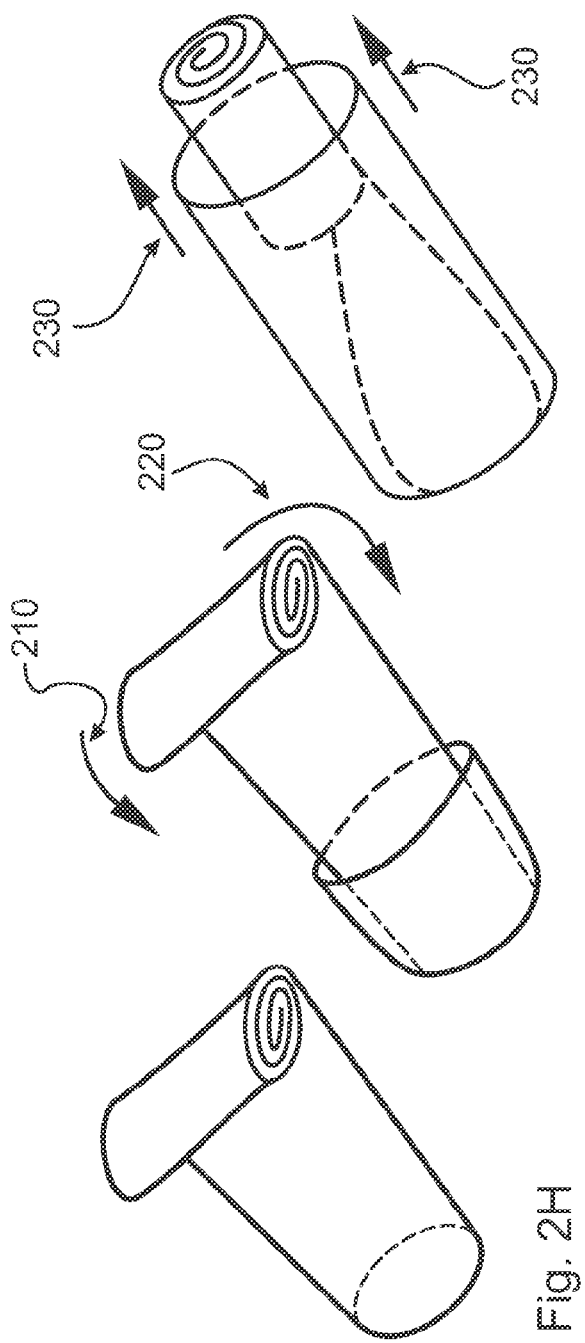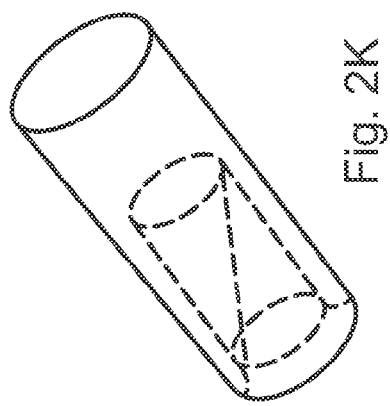

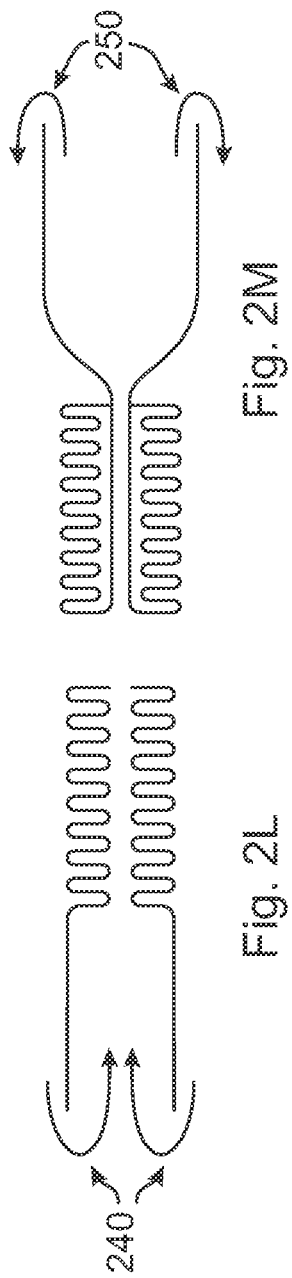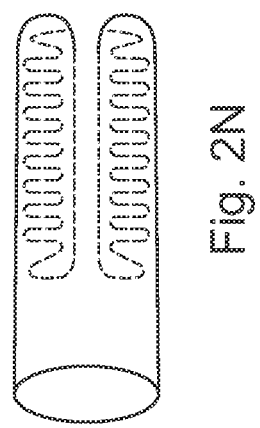

METHOD AND APPARATUS FOR EXTENDING A TUBE

This application is a continuation-in-part of U.S. application Ser. No. 13/695,033, filed Jan. 6, 2013, which is the U.S. national phase of International Application No. PCT/IL2010/000706, filed Aug. 29, 2010, which claims priority to U.S. Provisional Application No. 61/328,656, filed Apr. 28, 2010, the entire contents of each of which are hereby incorporated by reference.

FIELD OF THE INVENTION

The present invention relates generally to an apparatus and method for extending a tube, particularly suitable for colon cleansing devices and methods, and more specifically to colon cleansing by supplying washing liquid into the colon and collecting drain waste flowing out.

Furthermore, the present invention relates to propulsion of objects, namely flexible sleeves within curved lumens, namely the colon.

BACKGROUND OF THE INVENTION

There are many situations in which it is desired to insert a tube or pipe, particularly a flexible tube, into a relatively long and narrow channel or lumen or outer pipe. Such tube can be used to deliver fluids or an instrument to the end of the channel for medical and mechanical uses. At present, methods for such delivery include using guide wires or using tubes which are semi-rigid for ease of insertion. Common medical uses of such tubes include various endoscopic procedures, catheterization, and cleansing of the colon before performing colonoscopy examinations.

One of the most unpleasant and difficult stages of colonoscopy examination is the preparation of the patient prior to the examination. This preparation involves cleansing the patient's bowels and colon. During a colonoscopy procedure itself, patients are sedated so that they do not feel any pain, and sometimes do not even remember the test. However, the preparation is usually performed at home, and it can be quite challenging.

When using ingested laxatives, it can require the consumption of large volumes and/or of distasteful products. The exact laxative menu which is used varies according to the physician's or patient's experience, taste, and preference.

One consequence of this often unpleasant, and occasionally unsuccessful, preparation experience is that there are patients who undergo colonoscopy, the preparations for which are imperfect or suboptimal. Poor preparation impairs the detection of colonic neoplasms, particularly small lesions, but even large tumors can be missed due to solids in the colon under examination.

The main advantage of laxatives, used in the conventional method for colon cleansing, is that they cause cleansing in the normal direction of elimination of solids and liquids in the colon, that is, from the small intestine toward the anus. In this direction, the fecal matter is eliminated from the body, in a way similar to that in normal human bowel movement activity.

Mechanical cleansing methods, such as an enema and hydrotherapy irrigation, introduce fluids from the rectum in the direction of the small intestine, that is, in the direction opposite to the normal flow. These fluids are limited in their ability to reach far up the colon, and typically cleanse only about the lower third of the colon.

A number of prior art devices are known in the art which describe colonic cleansing in order to dislodge and remove fecal material from the patient's colon. These include: U.S. Pat. No. 4,182,332, which shows an insertable rectal catheter with a series of flanges contacting the rectal mucosal tissue. Such flanges would be likely to cause leakage, irritation, and infection of the tissue.

U.S. Pat. No. 4,067,335 provides a fecal matter collecting unit with an insertable funnel with a series of ribs contacting the rectal mucosal tissue. These ribs allow leakage and put too much pressure on the tissue adjacent to each rib, which could cause irritation and infection. U.S. Pat. No. 5,741,239 provides a fecal collection receptacle and tapered neck, a broad-lipped sealing ring with a bottom broad smooth flat sealing rim surface for contacting the rectal mucosal tissue that needs an external device for insertion and takes much space, causing an uncomfortable feeling in the rectal area.

U.S. Pat. No. 5,941,860 provides a fecal collector which comprises an elongated, flaccid pouch having an entrance end; an anchor attached to the pouch entrance end to anchor the entrance end in the lower bowel; and a positioner attached to the pouch in spaced relation to the anchor O-ring, to remain outside the lower bowel and adjacent to the body, for blocking tilting of the anchor in the bowel. This arrangement needs an external device for insertion and takes much space, which causes an uncomfortable feeling in the rectal area.

Lubricants or gels have been used to aid the insertion of devices through the rectum or anal canal area. U.S. Pat. No. 3,881,485 to Davis, Jr. ("Davis") discloses a device for insertion through the anus into the upper rectum for the purpose of wiping the walls of the rectum clean of feces and stopping and retaining feces in the colon and rectum at a distance from the anus. The invention is a preformed fiber device that is shaped for insertion through the anus into the upper rectum. The device is inserted through the anus and up through the rectum with a coating of non-irritating lubricant applied to the wiper. The lubricant should preferably be an organic, inert, water soluble gel, but other suitable lubricants may be used.

Other prior art patents disclose colon cleaning systems and methods that introduce an enema solution (i.e., preferably with a laxative) into the colon through the anal opening via a suitable tube held in the rectum by an inflated bladder or balloon. The balloon and a tube are introduced into the body of the patient (i.e., via the anus and to the rectum/colon). U.S. Pat. No. 4,403,982 to Clayton, U.S. Pat. No. 4,406,655 to Clayton, and U.S. Pat. No. 4,842,583 to Majlessi provide examples of such devices.

However, these bladder or balloon devices require regulation of the pressure to the bladder or balloon, and they have the problem of the possibility of injury occurring to the patient if the pressure is not regulated properly.

U.S. Pat. No. 5,049,138 to Chevalier et al. ("Chevalier") discloses a catheter having a tip that dissolves inside the body. The catheter includes a flexible tubular member that has an inner lumen and a rigid solid tip disposed at the end of the inner lumen. The tip (i.e. cone shaped) is formed of a material that is slippery when wet, soluble in bodily fluids and capable of absorbing radiographic fluids that are injected into the inner lumen for identification of the location of X-rays. A narrow passageway is disposed in the tip and is adapted to receive a guide wire for insertion of the catheter into an internal organ. Other devices include those disclosed in U.S. Pat. No. 6,984,226 of Abell et al, U.S. Pat. No. 5,190,519 of Mead et al, U.S. Pat. No. 5,176,630 of Shilling, et al., U.S. Pat. No. 5,405,319 of Abell et al., U.S.

Pat. No. 5,019,056 of Lee et al., and U.S. Pat. No. 4,874,363 of Abell. The primary purpose of each of these devices is the delivery of liquid into the colon through the anus of a patient for dislodging fecal material that may be lodged therein and then removing or draining the dislodged material along with the waste liquid from the colon to evacuate the bowels of the patient. Patent Application No. US 2007/0015965 of Cox et al, states that the cleansing of the colon for colonoscopy purposes needs to enter physically deep into the colon, however the method described uses a semi rigid tube, which is the same as performing an actual colonoscopy in parallel with or before the regular colonoscopy.

U.S. Pat. No. 6,988,988 discloses an apparatus for endoscopic inspection including an anchor unit for anchoring outside a body tract, a flexible sleeve coupled to the anchor and having a distal end fixed to an internal unit adapted to be propelled through the gastrointestinal tract. The sleeve is held initially in a compact state (accordion folds) in the internal unit and is arranged to feed out from the internal unit as the internal unit is advanced into the gastrointestinal tract. However, U.S. Pat. No. 6,988,988 provides an "internal unit" (or a probe) with a transparent optical window or lens and electro-optical package.

It was found by the inventors of the present invention that such an "internal unit" would have difficulties while navigating within the colon and most probably would be stuck and jammed within the colon (due to friction forces between the colon and the unit) instead of navigating throughout the same.

According to U.S. Pat. No. 6,988,988, in order to ease navigation of the "internal unit" through the colon, the same is provided with a steering unit. Such steering unit enlarges the dimensions of the "internal unit" and further increases the difficulties in navigation thought the colon.

Thus, there still remains a long felt need for an endoscopic apparatus which will enable easy navigation while minimizing the friction forces.

Furthermore, there is still a need for patient-friendly yet efficient colon cleansing devices and methods that overcome the limitations of the prior art devices and methods. In particular, there is a need for an easy yet efficient method for washing a colon in the direction from the cecum towards the anus.

Delivery of a contrast agent, such as barium sulfate, into the colon is well known. Also known is combined delivery of gas and contrast agent, see U.S. Pat. No. 5,322,070. However, control over which specific portion of the colon is filled with barium remains limited. Furthermore, at present, in case of combined delivery of both barium and gas into the colon, one problem is how to control the properties of the barium coating of the colon wall, when the colon is filled with gas.

Conventional endoscopy uses cameras for imaging, often by way of taking two-dimensional pictures. Three-dimensional imaging in endoscopy is also known. See, for example, U.S. Pat. Nos. 6,503,195, 6,798,570, 6,949,069, 6,749,346, 6,563,105, 5,751,341, 5,673,147. A need exists for delivery of a camera into a lumen of a patient using a simple and self-guided technique. Also, after delivery, a need exists for providing images of the lumen in a simple and informative way.

SUMMARY OF THE INVENTION

It is one object of the present invention to provide an endoscopic apparatus reversibly insertable into a curved lumen of a patient, comprising:

a. a flexible sleeve characterized by a proximal end and a distal end; the distal end of the flexible sleeve comprising:
  i. a flexible folded sleeve part comprising at least a portion of the flexible sleeve in a compact and folded arrangement, such that a compact and folded sleeve portion is enclosed within the folded sleeve part; the compact and folded sleeve portion is adapted to unfold and evert at least a portion of the compact and folded sleeve portion, as the same is advanced within the curved lumen of the patient; the folded sleeve part is characterized by a predetermined length $L_{fold}$; and
  ii. an unfolded sleeve portion in communication with the compact folded sleeve part; the unfolded sleeve portion is characterized by a length $L_{unfold}$; the $L_{unfold}$ increases as at least a portion of the compact and folded sleeve portion unfolds and everts;
    wherein the compact and folded sleeve portion is enclosed and within the folded sleeve part such that a single topologically cylindrical sleeve is provided;
    further wherein the enclosing of the compact and folded sleeve portion within the folded sleeve part is provided such that the flexible folded sleeve part advances with the curved lumen when at least a portion of the compact and folded sleeve portion unfolds and everts; further wherein the eversion is provided so as to increase the unfolded sleeve portion length $L_{unfold}$ and such that the flexible folded sleeve part self-navigates within the curved lumen.

It is another object of the present invention to provide the endoscopic apparatus as defined above, wherein the predetermined length $L_{fold}$ remains substantially the same when fluid is introduced into the folded sleeve part so as to evert and unfold at least a portion of the compact folded portion as the same advances within the curved lumen, such that longitudinal shearing forces between (a) at least one selected from a group consisting of (i) the folded sleeve part, (ii) the unfolded sleeve portion, and (iii) any combination thereof; and (b) the curved lumen is mitigated so as to enable advancement of the folded sleeve part within the curved lumen.

It is another object of the present invention to provide the endoscopic apparatus as defined above, wherein at least one of the following is being held true:
  (a) the predetermined length $L_{fold}$ remains substantially the same when fluid is introduced into the flexible folded sleeve part casing and the compact and folded sleeve portion unfolds and everts;
  (b) the unfolded sleeve portion length $L_{unfold}$ increases as at least a portion of the compact and folded sleeve portion unfolds and everts,
  such that longitudinal shearing forces between (a) at least one selected from a group consisting of (i) the folded sleeve casing, (ii) the unfolded sleeve portion, and (iii) any combination thereof; and (b) the curved lumen is mitigated.

It is another object of the present invention to provide the endoscopic apparatus as defined above, wherein the unfolding of at least a portion of the compact and folded sleeve portion is characterized by an unfolding function Y calculated as the ratio $L_{unfold}/L_{fold}$ as a function of time t, Y(t) represented by at least 2 regions:
  a. at least one first region 0<t<x1; in which Y(t) substantially equals 1;

b. at least one second region t>x1; in which Y(t) is greater than 1.

It is another object of the present invention to provide the endoscopic apparatus as defined above, additionally comprising fluid input means, in fluid communication with the folded sleeve part, adapted to introduce fluid into the same so as to unfold at least part of the compact folded portion; further wherein the fluid is selected from a group consisting of gas, liquid and any combination thereof.

It is another object of the present invention to provide the endoscopic apparatus as defined above, additionally comprising an inflating tube, coupled to the unfolded sleeve portion, adapted to inflate at least a portion of the compact and folded sleeve portion.

It is another object of the present invention to provide the endoscopic apparatus as defined above, further wherein the tube is adapted to deflate the flexible sleeve for withdrawal of the same from the curved lumen.

It is another object of the present invention to provide the endoscopic apparatus as defined above, wherein the curved lumen is the gastrointestinal tract.

It is another object of the present invention to provide the endoscopic apparatus as defined above, wherein the apparatus is adapted for cleansing a colon of a patient.

It is another object of the present invention to provide the endoscopic apparatus as defined above, wherein the endoscopic apparatus is adapted to enable inspection of the curved lumen.

It is another object of the present invention to provide the endoscopic apparatus as defined above, wherein the compact and folded arrangement of the compact and folded sleeve portion is selected from a group consisting of telescopic arrangement, accordion arrangement, zigzag arrangement, spiral-like folding arrangement and any combination thereof.

It is another object of the present invention to provide the endoscopic apparatus as defined above, wherein at least one of the following is being held true (a) the cross section of the flexible folded sleeve part is a constant cross section along the length of the same; (b) the cross section of the flexible folded sleeve part is a varied cross section along the length of the same; (c) at least a part of the flexible folded sleeve part has a cross-section that is quasi-periodically variable along the length of the flexible sleeve; (d) at least a part of the cross section of the flexible folded sleeve part is a sausage-chain-like cross section, a bead-string-like cross section and any combination thereof; and any combination thereof.

It is another object of the present invention to provide the endoscopic apparatus as defined above, wherein the diameter of the flexible sleeve does not alter when the same is inflated.

It is another object of the present invention to provide the endoscopic apparatus as defined above, wherein the flexible sleeve additionally comprises at least one aperture.

It is another object of the present invention to provide the endoscopic apparatus as defined above, wherein the flexible sleeve is adapted for cleansing the lumen, such that cleansing fluids exit and outflow from the aperture.

It is another object of the present invention to provide the endoscopic apparatus as defined above, additionally comprising a removable cap adapted to ease the insertion of the flexible sleeve into the lumen.

It is another object of the present invention to provide the endoscopic apparatus as defined above, wherein the removable cap is filled with water.

It is another object of the present invention to provide the endoscopic apparatus as defined above, wherein the removable cap is made of a material that would melt, soften, dissolve and any combination thereof upon being inserted into the lumen.

It is another object of the present invention to provide the endoscopic apparatus as defined above, wherein the removable cap comprises several segments, each of which is small enough to be pulled back through the flexible sleeve with a flow of liquid.

It is another object of the present invention to provide the endoscopic apparatus as defined above, wherein the flexible sleeve is made of materials selected from a group consisting of polyethylene (preferably low density polyethylene), polypropylene, polyurethane and any combination thereof.

It is another object of the present invention to provide the endoscopic apparatus as defined above, wherein the flexible sleeve is designed and constructed so as to enable the insertion of an endoscope into the same.

It is another object of the present invention to provide the endoscopic apparatus as defined above, wherein the flexible sleeve is designed and constructed so as to enable the insertion of an object into the same.

It is another object of the present invention to provide the endoscopic apparatus as defined above, wherein the object is selected from a group consisting of a camera, a detachable capsule, a source of radiation, a source of light, a source of X-rays, a source of positrons, a source of other radioactivity, and any combination thereof.

It is another object of the present invention to provide the endoscopic apparatus as defined above, wherein the object is coupled directly to the flexible sleeve.

It is another object of the present invention to provide the endoscopic apparatus as defined above, wherein the object is introduced into the flexible sleeve after the same has been fully extended within the lumen.

It is another object of the present invention to provide the endoscopic apparatus as defined above, wherein the object is introduced into the flexible sleeve while the same is not fully extended within the lumen, such that the object advances with the flexible sleeve.

It is another object of the present invention to provide the endoscopic apparatus as defined above, wherein the flexible sleeve is characterized by at least one wider section of the same.

It is another object of the present invention to provide the endoscopic apparatus as defined above, wherein the at least one wider section is adapted to spread the wall of the lumen so as to enable visual examination of the same.

It is another object of the present invention to provide the endoscopic apparatus as defined above, wherein a plurality of cameras are coupled to at least one location of the flexible sleeve.

It is another object of the present invention to provide the endoscopic apparatus as defined above, wherein a plurality of cameras is introduced into the flexible sleeve.

It is another object of the present invention to provide the endoscopic apparatus as defined above, wherein at least one contrast agent adapted for medical imaging of the lumen is introduced into the flexible sleeve.

It is another object of the present invention to provide the endoscopic apparatus as defined above, wherein the at least one contrast agent is introduced once the flexible sleeve is fully extended.

It is another object of the present invention to provide the endoscopic apparatus as defined above, wherein the at least one contrast agent is selected from a group consisting of barium sulfate, water soluble contrast agents and any combination thereof.

It is another object of the present invention to provide the endoscopic apparatus as defined above, wherein at least one medication is introduced through the flexible sleeve into the lumen.

It is another object of the present invention to provide the endoscopic apparatus as defined above, wherein the flexible sleeve is adapted to massage at least a part of the wall of the lumen.

It is another object of the present invention to provide the endoscopic apparatus as defined above, wherein the flexible sleeve conforms to the walls of the lumen so as to massage the same.

It is another object of the present invention to provide the endoscopic apparatus as defined above, wherein at least a portion of the flexible sleeve is characterized by a narrower cross sectional area.

It is another object of the present invention to provide the endoscopic apparatus as defined above, wherein at least one selected from a group consisting of the folded sleeve portion, the unfolded sleeve portion and any combination thereof additionally comprises at least one element selected from a group consisting of at least one camera adapted to provide either 2D or 3D real time images, an ultrasound sensor, a source of ultrasound, a radiation sensor, a source of radiation and any combination thereof.

It is another object of the present invention to provide the endoscopic apparatus as defined above, wherein a piston is introduced into the flexible sleeve and is propelled inside the same by pressure of a fluid being pumped into the flexible sleeve.

It is another object of the present invention to provide the endoscopic apparatus as defined above, wherein the piston is coupled to an object.

It is another object of the present invention to provide the endoscopic apparatus as defined above, wherein the piston is in communication with an object.

It is another object of the present invention to provide the endoscopic apparatus as defined above, wherein the object is selected from a group consisting of at least one camera adapted to provide either 2D or 3D real time images, an ultrasound sensor, a source of ultrasound, a radiation sensor, a source of radiation and any combination thereof.

It is another object of the present invention to provide the endoscopic apparatus as defined above, wherein the object is a camera; further wherein the camera is adapted to take images while the flexible sleeve is being withdrawn from the lumen; the image being used for visual inspection of space around the camera upon recording the image, in real time and any combination thereof.

It is another object of the present invention to provide the endoscopic apparatus as defined above, wherein the flexible sleeve comprises at least one opening through which the camera has a view unobstructed by the flexible sleeve.

It is another object of the present invention to provide the endoscopic apparatus as defined above, wherein the advance of the piston is stopped by a prepositioned obstacle at a position appropriate for subsequent functioning of the piston.

It is another object of the present invention to provide the endoscopic apparatus as defined above, additionally comprising a drainage channel adapted for insertion into a lumen, the flexible sleeve disposed inside and extending through the drainage channel and the lumen, whereby washing liquid is drained out of the lumen through the drainage channel.

It is another object of the present invention to provide the endoscopic apparatus as defined above, additionally comprising at least one inflatable balloon coupled to the drainage channel; the balloon is inflated inside the lumen; the inflated balloon together with the drainage channel maintains the drainage channel in position and prevents any unwanted movements.

It is another object of the present invention to provide the endoscopic apparatus as defined above, additionally comprising a delivery tube characterized by a distal end and a proximal end interconnected to one another by a hollow bore, said delivery tube fluidly connectable at its distal end to said proximal end of said flexible sleeve.

It is another object of the present invention to provide the endoscopic apparatus as defined above wherein said delivery tube is substantially cylindrical.

It is another object of the present invention to provide the endoscopic apparatus as defined above, wherein said delivery tube is removably attachable to said proximal end of flexible sleeve.

It is another object of the present invention to provide the endoscopic apparatus as defined above, additionally comprising an attachment means, located at said distal end of said delivery tube; adapted to provide attachment between said distal end of said delivery tube and said proximal end of said flexible sleeve.

It is another object of the present invention to provide the endoscopic apparatus as defined above, wherein said attachment means is selected from a group consisting of: an elastic band, an elastic tie, a ribbon, a tape, a catch, a clip and any combination thereof.

It is another object of the present invention to provide the endoscopic apparatus as defined above, additionally comprising a flange located at said distal end of said delivery tube, said flange is unitary with said distal end of said delivery tube, said distal end wider than said proximal end.

It is another object of the present invention to provide the endoscopic apparatus as defined above, wherein the shape of said flange is selected from a group consisting of substantially conical, substantially spherical, substantially ellipsoidal, substantially ovoid, substantially hyperboloid, and any combination thereof.

It is another object of the present invention to provide the endoscopic apparatus as defined above, wherein the diameter of said flange is in the range of approximately 2 times the diameter of said delivery tube to approximately 5 times said diameter of said delivery tube.

It is another object of the present invention to provide the endoscopic apparatus as defined above, wherein said hollow bore is adapted to deliver at least one fluid to unfold and evert at least a portion of said compact and folded sleeve portion.

It is another object of the present invention to provide the endoscopic apparatus as defined above, wherein said fluid is selected from a group consisting of a liquid, a gas and any combination thereof.

It is another object of the present invention to provide the endoscopic apparatus as defined above, wherein said liquid comprises members of a group consisting of saline, water, washing liquid, sodium phosphate, baking soda, barium compounds, mineral oil, glycerin, laxatives, medicaments, and any combination thereof.

It is another object of the present invention to provide the endoscopic apparatus as defined above, wherein said gas is selected from a group consisting of air, nitrogen, oxygen, CO2, xenon and any combination thereof.

It is another object of the present invention to provide a method of extending a tube within a curved lumen; comprising steps of:

a. obtaining a flexible sleeve, comprising
  i. a flexible folded sleeve part comprising at least a portion of the flexible sleeve in a compact and folded arrangement, such that a compact and folded sleeve portion is enclosed within the folded sleeve part; the compact and folded sleeve portion is adapted to unfold and evert at least a portion of the compact and folded sleeve portion, as the same is advanced within the curved lumen of the patient; the folded sleeve part is characterized by a predetermined length $L_{fold}$; and
  ii. an unfolded sleeve portion in communication with the compact folded sleeve part; the unfolded sleeve portion characterized by a length $L_{unfold}$; $L_{unfold}$ increases as at least a portion of the compact and folded sleeve portion unfolds and everts;
  wherein the compact and folded sleeve portion is enclosed and within the folded sleeve part such that a single topologically cylindrical sleeve is provided; further wherein the enclosing of the compact and folded sleeve portion within the folded sleeve part is provided such that the flexible folded sleeve part advances with the curved lumen when at least a portion of the compact and folded sleeve portion unfolds and everts; further wherein the eversion is provided so as to increase the unfolded sleeve portion length $L_{unfold}$ and such that the flexible folded sleeve part self-navigates within the curved lumen
b. inserting the flexible sleeve into the lumen;
c. introducing a fluid into the flexible folded sleeve part, thereby unfolding and everting at least a portion of the compact and folded sleeve portion; and
d. extending the flexible sleeve within the curved lumen.

It is another object of the present invention to provide the method as defined above, wherein the predetermined length $L_{fold}$ remains substantially the same when fluid is introduced into the folded sleeve part so as to evert and unfold at least a portion of the compact folded portion as the same advances within the curved lumen, such that longitudinal shearing forces between (a) at least one selected from a group consisting of (i) the folded sleeve part, (ii) the unfolded sleeve portion, and (iii) any combination thereof; and (b) the curved lumen is mitigated so as to enable advancement of the folded sleeve part within the curved lumen.

It is another object of the present invention to provide the method as defined above, wherein at least one of the following is being held true:
a. the predetermined length $L_{fold}$ remains substantially the same when fluid is introduced into the flexible folded sleeve part casing and the compact and folded sleeve portion unfolds and everts;
b. the predetermined length $L_{unfold}$ increases as at least a portion of the compact and folded sleeve portion unfolds and everts,
such that longitudinal shearing forces between (a) at least one selected from a group consisting of (i) the folded sleeve casing, (ii) the unfolded sleeve portion, and (iii) any combination thereof; and (b) the curved lumen is mitigated.

It is another object of the present invention to provide the method as defined above, wherein the unfolding of at least a portion of the compact and folded sleeve portion is characterized by an unfolding function Y calculated as the ratio $L_{unfold}/L_{fold}$ as a function of time t, Y(t) represented by at least 2 regions:
  a. at least one first region 0<t<x1; in which Y(t) substantially equals 1;
  b. at least one second region t>x1; in which Y(t) is greater than 1.

It is another object of the present invention to provide the method as defined above, additionally comprising a step of providing the endoscopic apparatus with fluid input means, in fluid communication with the folded sleeve part, adapted to introduce fluid into the same so as to unfold at least part of the compact folded portion.

It is another object of the present invention to provide the method as defined above, wherein the fluid is selected from a group consisting of gas, liquid and any combination thereof.

It is another object of the present invention to provide the method as defined above, additionally comprising a step of providing the endoscopic apparatus with an inflating tube, coupled to the unfolded sleeve portion, adapted to inflate at least a portion of the compact and folded sleeve portion.

It is another object of the present invention to provide the method as defined above, wherein the tube is adapted to deflate the flexible sleeve for withdrawal of the same from the curved lumen.

It is another object of the present invention to provide the method as defined above, wherein the curved lumen is the gastrointestinal tract and the colon of a patient.

It is another object of the present invention to provide the method as defined above, wherein the apparatus is adapted for cleansing a colon of a patient.

It is another object of the present invention to provide the method as defined above, wherein the endoscopic apparatus is adapted to enable inspection of the curved lumen.

It is another object of the present invention to provide the method as defined above, wherein the compact and folded arrangement of the compact and folded sleeve portion is selected from a group consisting of telescopic arrangement, accordion arrangement, spiral-like rolled arrangement, zigzag arrangement and any combination thereof.

It is another object of the present invention to provide the method as defined above, wherein the cross section of the flexible folded sleeve part is a constant cross section along the length of the same.

It is another object of the present invention to provide the method as defined above, wherein the cross section of the flexible folded sleeve part is a varied cross section along the length of the same.

It is another object of the present invention to provide the method as defined above, wherein at least a part of the flexible folded sleeve part has a cross-section that is quasi-periodically variable along the length of the flexible sleeve.

It is another object of the present invention to provide the method as defined above, wherein at least a part of the cross section of theflexible folded sleeve part is a sausage-chain-like cross section, a bead-string-like cross section and any combination thereof.

It is another object of the present invention to provide the method as defined above, additionally comprising a step of setting the diameter of the flexible sleeve such that the diameter does not alter when the flexible sleeve is inflated.

It is another object of the present invention to provide the method as defined above, additionally comprising a step of providing the flexible sleeve with at least one aperture.

It is another object of the present invention to provide the method as defined above, wherein the flexible sleeve is adapted for cleansing the lumen, such that cleansing fluids exits and outflow from the aperture.

It is another object of the present invention to provide the method as defined above, additionally comprising a step of providing the flexible sleeve with a removable cap adapted to ease the insertion of the flexible sleeve into the lumen.

It is another object of the present invention to provide the method as defined above, wherein the removable cap is filled with water.

It is another object of the present invention to provide the method as defined above, wherein the removable cap is made of a material that would melt, soften, dissolve and any combination thereof upon being inserted into the lumen.

It is another object of the present invention to provide the method as defined above, wherein the removable cap comprises several segments, each of which is small enough to be pulled back through the flexible sleeve with a flow of liquid.

It is another object of the present invention to provide the method as defined above, wherein the flexible sleeve is made of materials selected from a group consisting of polyethylene (preferably low density polyethylene), polypropylene, polyurethane and any combination thereof.

It is another object of the present invention to provide the method as defined above, additionally comprising a step of designing and constructing the flexible sleeve so as to enable the insertion of an endoscope into the same.

It is another object of the present invention to provide the method as defined above, additionally comprising a step of designing and constructing the flexible sleeve so as to enable the insertion of an object into the same.

It is another object of the present invention to provide the method as defined above, wherein the object is selected from a group consisting of a camera, a detachable capsule, a source of radiation, a source of light, a source of X-rays, a source of positrons, a source of other radioactivity, and any combination thereof.

It is another object of the present invention to provide the method as defined above, wherein the object is coupled directly to the flexible sleeve.

It is another object of the present invention to provide the method as defined above, wherein the object is introduced into the flexible sleeve after the same has been fully extended within the lumen.

It is another object of the present invention to provide the method as defined above, wherein the object is introduced into the flexible sleeve while the same is not fully extended within the lumen, such that the object advances with the flexible sleeve.

It is another object of the present invention to provide the method as defined above, wherein the flexible sleeve is characterized by at least one wider section.

It is another object of the present invention to provide the method as defined above, wherein the at least one wider section is adapted to spread the wall of the lumen so as to enable visual examination of the same.

It is another object of the present invention to provide the method as defined above, additionally comprising a step of coupling a plurality of cameras to at least one location of the flexible sleeve.

It is another object of the present invention to provide the method as defined above, additionally comprising a step of introducing a plurality of cameras into the flexible sleeve.

It is another object of the present invention to provide the method as defined above, additionally comprising a step of introducing at least one contrast agent adapted for medical imaging of the lumen into the flexible sleeve.

It is another object of the present invention to provide the method as defined above, wherein the at least one contrast agent is introduced once the flexible sleeve is fully extended.

It is another object of the present invention to provide the method as defined above, wherein the at least one contrast agent is selected from a group consisting of barium sulfate, water soluble contrast agents and any combination thereof.

It is another object of the present invention to provide the method as defined above, additionally comprising a step of introducing at least one medication through the flexible sleeve into the lumen.

It is another object of the present invention to provide the method as defined above, additionally comprising a step of massaging at least a part of the wall of the lumen.

It is another object of the present invention to provide the method as defined above, wherein the flexible sleeve conforms to the walls of the lumen so as to massage the same.

It is another object of the present invention to provide the method as defined above, additionally comprising a step of providing the flexible sleeve with at least a portion of the same being characterized by a narrower cross sectional area.

It is another object of the present invention to provide the method as defined above, wherein at least one selected from a group consisting of the folded sleeve portion, the unfolded sleeve portion and any combination thereof additionally comprises at least one element selected from a group consisting of at least one camera adapted to provide either 2D or 3D real time images, an ultrasound sensor, a source of ultrasound, a radiation sensor, a source of radiation and any combination thereof.

It is another object of the present invention to provide the method as defined above, additionally comprising a step of introducing a piston into the flexible sleeve and propelling the same inside the flexible sleeve by pressure of a fluid being pumped into the flexible sleeve.

It is another object of the present invention to provide the method as defined above, wherein the piston is coupled to an object.

It is another object of the present invention to provide the method as defined above, wherein the piston is in communication with an object.

It is another object of the present invention to provide the method as defined above, wherein the object is selected from a group consisting of at least one camera adapted to provide either 2D or 3D real time images, an ultrasound sensor, a source of ultrasound, a radiation sensor, a source of radiation and any combination thereof.

It is another object of the present invention to provide the method as defined above, wherein the object is a camera; further wherein the camera is adapted to take images while the flexible sleeve is being withdrawn from the lumen; the image being used for visual inspection of space around the camera upon recording the image, in real time and any combination thereof.

It is another object of the present invention to provide the method as defined above, wherein the flexible sleeve comprises at least one opening through which the camera has a view unobstructed by the flexible sleeve.

It is another object of the present invention to provide the method as defined above, wherein the advance of the piston is stopped by a prepositioned obstacle at a position appropriate for subsequent functioning of the piston.

It is another object of the present invention to provide the method as defined above, additionally comprising a drainage channel adapted for insertion into a lumen, the flexible sleeve disposed inside and extending through the drainage channel and the lumen, whereby washing liquid is drained out of the lumen through the drainage channel.

It is another object of the present invention to provide the method as defined above, additionally comprising at least one inflatable balloon coupled to the drainage channel; the balloon inflated inside the lumen; the inflated balloon together with the drainage channel maintaining the drainage channel in position and preventing any unwanted movements.

It is another object of the present invention to provide the method as defined above, additionally comprising a delivery tube characterized by a distal end and a proximal end interconnected to one another by a hollow bore, said delivery tube fluidly connectable at its distal end to said proximal end of said flexible sleeve.

It is another object of the present invention to provide the method as defined above, additionally comprising a step of selecting said delivery tube to be substantially cylindrical.

It is another object of the present invention to provide the method as defined above, additionally comprising a step of providing said delivery tube removably attachable to said proximal end of flexible sleeve.

It is another object of the present invention to provide the method as defined above, additionally comprising an attachment means, located at said distal end of said delivery tube; adapted to provide attachment between said distal end of said delivery tube and said proximal end of said flexible sleeve.

It is another object of the present invention to provide the method as defined above, additionally comprising a step of selecting said attachment means from a group consisting of: an elastic band, an elastic tie, a ribbon, a tape, a catch, a clip and any combination thereof.

It is another object of the present invention to provide the method as defined above, additionally comprising a step of providing a flange located at said distal end of said delivery tube, said flange is unitary with said distal end of said delivery tube, said distal end wider than said proximal end.

It is another object of the present invention to provide the method as defined above, additionally comprising a step of selecting the shape of said flange from a group consisting of substantially conical, substantially spherical, substantially ellipsoidal, substantially ovoid, substantially hyperboloid, and any combination thereof.

It is another object of the present invention to provide the method as defined above, additionally comprising a step of selecting the diameter of said flange to be in the range of approximately 2 times the diameter of said delivery tube to approximately 5 times said diameter of said delivery tube.

It is another object of the present invention to provide the method as defined above, additionally comprising a step of adapting said hollow bore to deliver at least one fluid to unfold and evert at least a portion of said compact and folded sleeve portion.

It is another object of the present invention to provide the method as defined above, additionally comprising a step of selecting said fluid from a group consisting of a liquid, a gas and any combination thereof.

It is another object of the present invention to provide the method as defined above, additionally comprising a step of comprising said liquid of members of a group consisting of saline, water, washing liquid, sodium phosphate, baking soda, barium compounds, mineral oil, glycerin, laxatives, medicaments, and any combination thereof.

It is another object of the present invention to provide the method as defined above, additionally comprising a step of selecting said gas from a group consisting of air, nitrogen, oxygen, $CO_2$, xenon and any combination thereof.

It is another object of the present invention to provide a method of assembling a flexible folded sleeve part, comprising steps of:
(a) providing a flexible sleeve, said flexible sleeve having a longitudinal axis, a proximal end and a distal end;
(b) rolling a portion of said flexible sleeve into a spiral-like structure, starting from said proximal end;
(c) rotating said spiral-like structure such that the axis of said spiral-like structure is parallel to said longitudinal axis of said flexible sleeve; and
(d) fully inverting said flexible sleeve, starting from said proximal end; thereby enclosing at least a portion of said spiral-like structure within said flexible sleeve.

It is another object of the present invention to provide a method of assembling a flexible folded sleeve part comprising steps of:
(a) providing a flexible sleeve, said flexible sleeve having a longitudinal axis, a proximal end and a distal end;
(b) folding a portion of said flexible sleeve into a zigzag structure, starting from said distal end;
(c) inverting said proximal end of said flexible sleeve and passing said inverted proximal end through the lumen of said zigzag structure; and
(d) inverting said proximal end of said flexible sleeve and passing said inverted proximal end over the outside of said zigzag structure; thereby enclosing a portion of said flexible sleeve within said zigzag structure and further enclosing at least a portion of said zigzag structure within said flexible sleeve wherein said zigzag structure remains compact during eversion.

BRIEF DESCRIPTION OF THE DRAWINGS

The invention will now be described in connection with certain preferred embodiments, illustrating colon cleansing, for which it is particularly suited, by way of non-limiting example, with reference to the following illustrative figures so that it may be more fully understood.

With specific reference now to the Figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1B illustrate the friction forces of the sleeve within a straight lumen (see FIG. 1A) and within a curved lumen (see FIG. 1B);

FIG. 1C is a schematic illustration of a tube partially inserted through a lumen, constructed and operative in accordance with the present invention;

FIGS. 2A, 2B and 2C are schematic cross-sectional illustrations of a folded feed tube inside its container, in accordance with different embodiments of the present invention;

FIG. 2D is a schematic side view illustration of a feed tube inserted into a drainage channel with the help of a straw-like tube, in accordance with some embodiments of the present invention;

FIGS. 2E, 2E-1, 2E-2, 2E-3, 2E-4 are schematic views of part of a feed tube, showing the distal end of a straw-like tube and the proximal end of a flexible sleeve;

FIG. 2F is a schematic illustration of a telescopic folding arrangement of the compact and folded sleeve portion 19;

FIG. 2G is a schematic illustration of a spiral-like folding arrangement of the compact and folded sleeve portion 19;

FIGS. 2H, 2I, 2J and 2K are schematic illustrations of a method of assembling a spiral-like rolled arrangement of the compact and folded sleeve portion 19;

FIGS. 2L, 2M and 2N are schematic illustrations of a method of assembling a zigzag-like arrangement of the compact and folded sleeve portion 19;

FIG. 3A is a schematic cross-sectional illustration of an unfolding feed tube which has been packed in a concentric zigzag manner, in accordance with an embodiment of the present invention;

FIG. 3B is a schematic cross-sectional illustration of an unfolding feed tube which was packed in an up and down zigzag manner, in accordance with an embodiment of the present invention;

Figure 4:
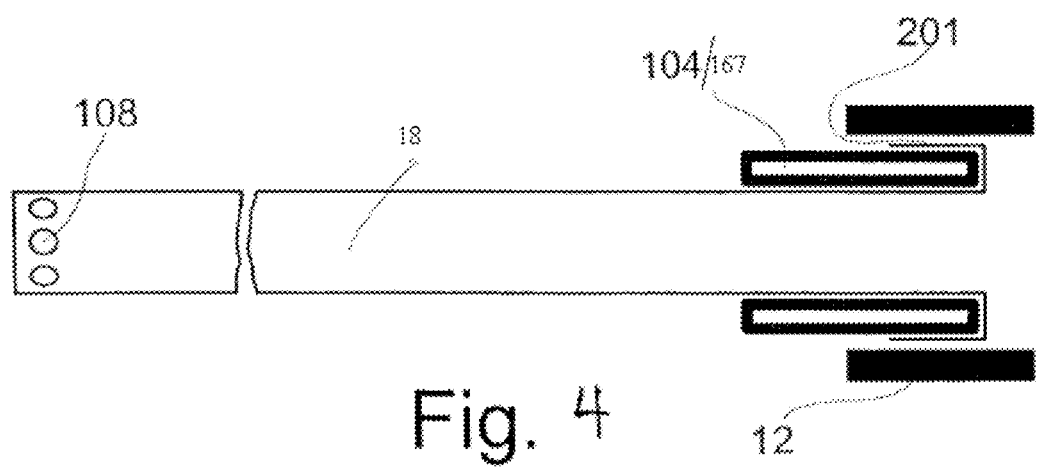
Figure 6:
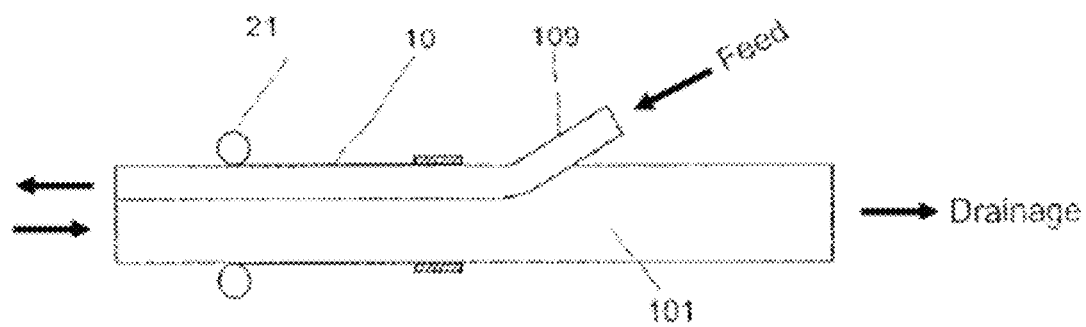
Figure 7A:
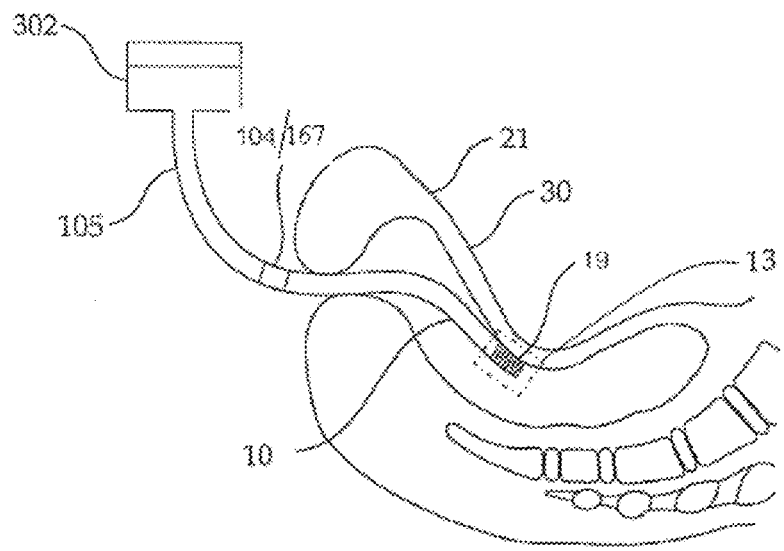
Figure 7B:
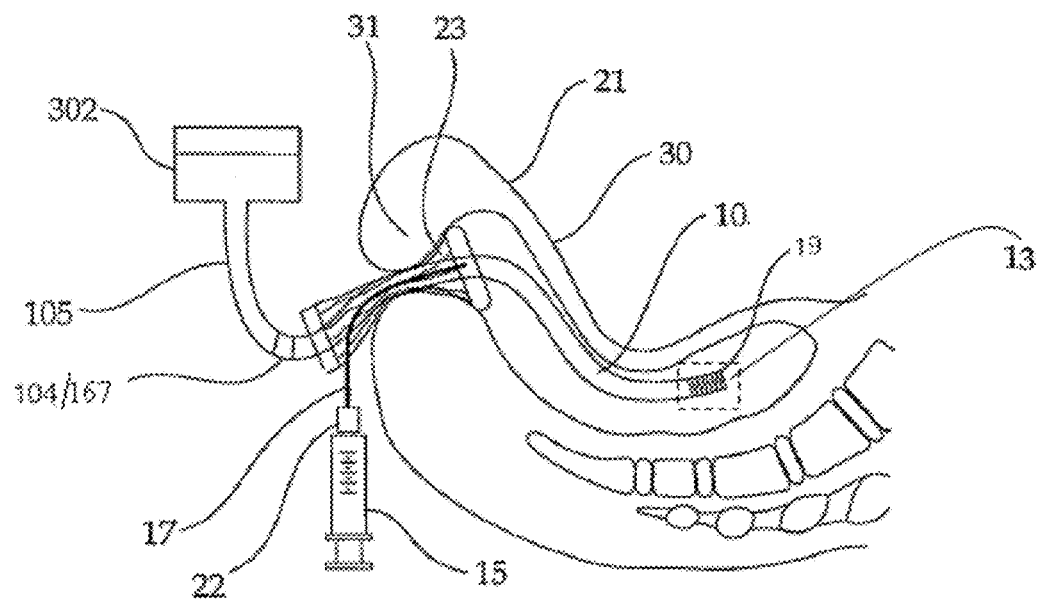
Figure 7C:
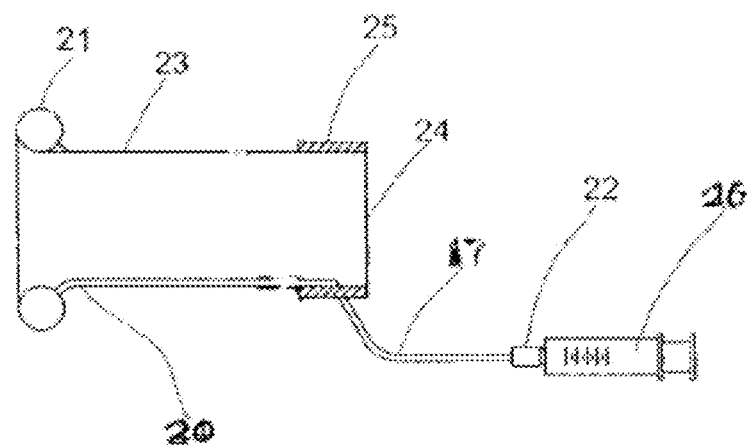
Figure 8:
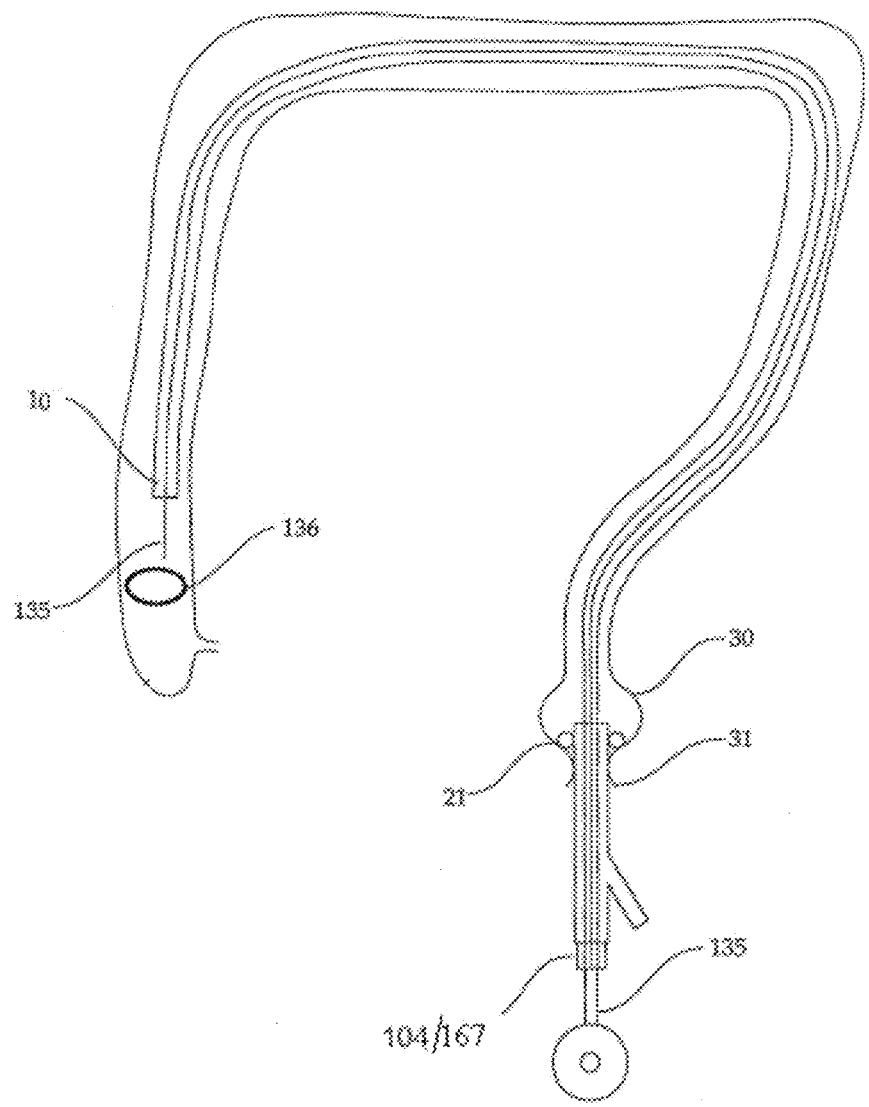
Figure 9:
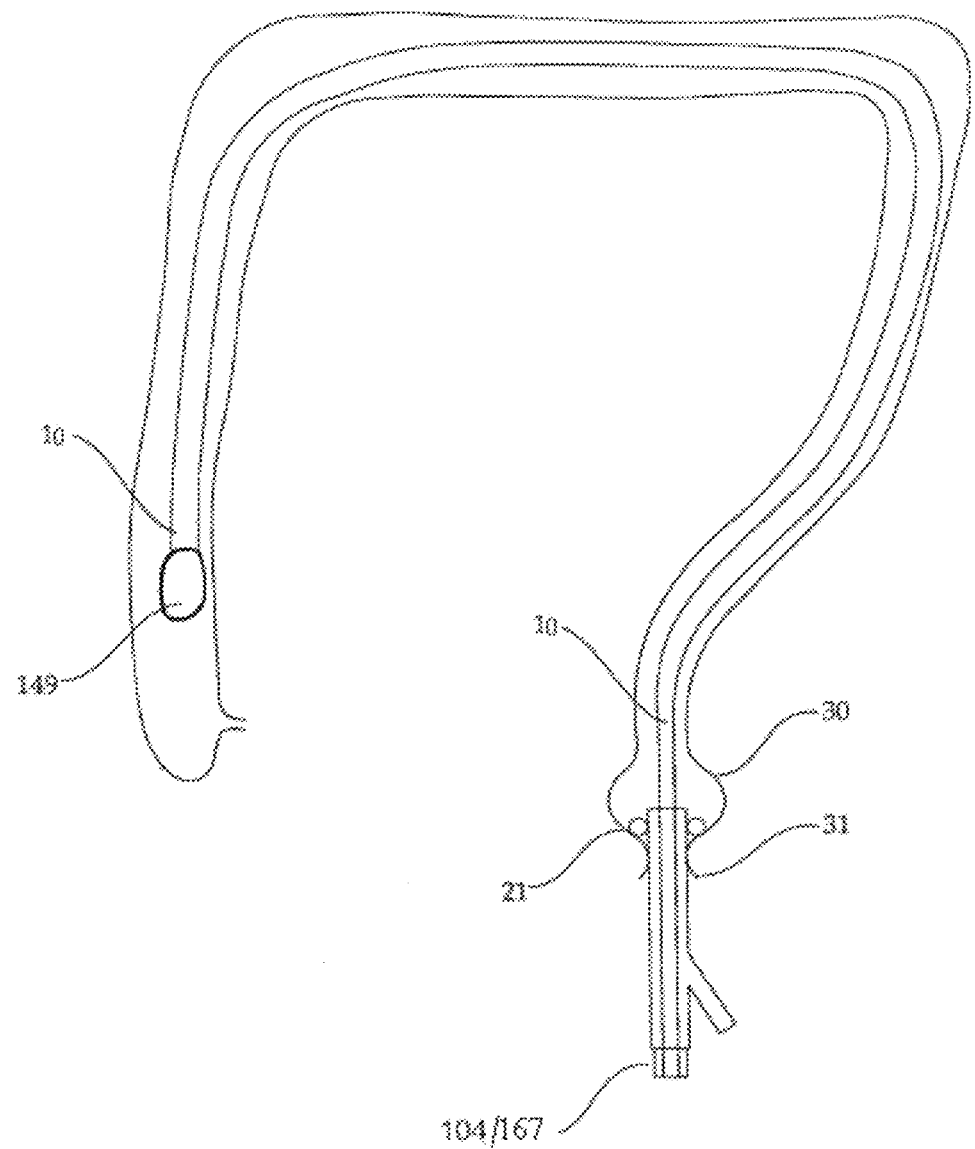
Figure 10:
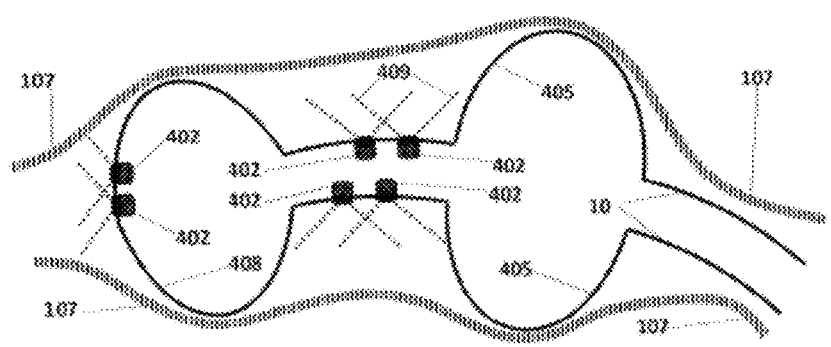
Figure 11:
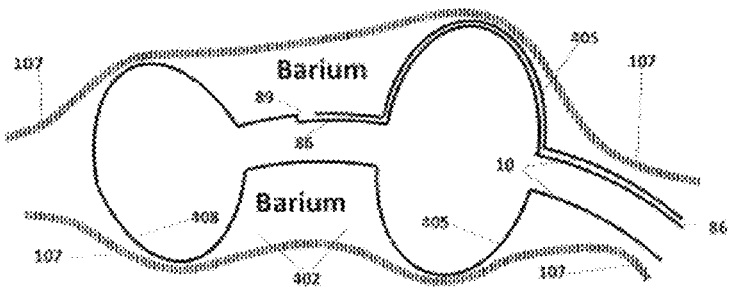
Figure 12:
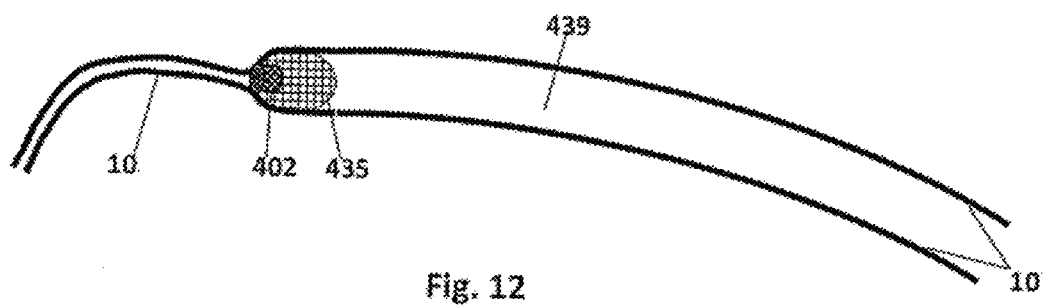
Figure 13:
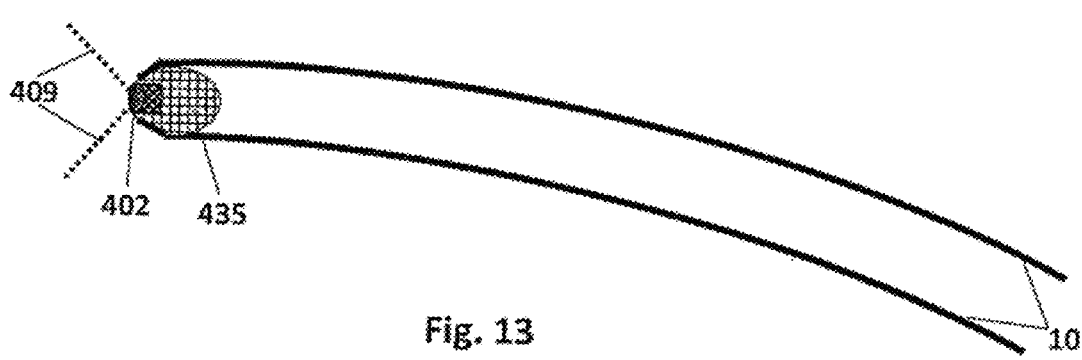

FIG. 4 is a schematic side view illustration of a fully unfolded feed tube, in accordance with an embodiment of the present invention;

FIGS. 5A-5E are schematic illustrations of five stages of insertion of the apparatus into the colon, in accordance with an embodiment of the present invention; FIGS. 5A to 5E schematically illustrate several embodiments of the proposed methods of colon cleansing and the devices involved;

FIG. 6 is a schematic illustration of a device according to the present invention, showing inflow of feed fluid and the outflow of drainage;

FIGS. 7A-7C are schematic illustrations of a side view of the system with the following variations: FIG. 7A shows a feed tube alone, without any drainage channel in accordance with an embodiment of the present invention; FIG. 7B shows a feed tube with a soft drainage channel that carries an inflated balloon for keeping the channel in the anus in accordance with an embodiment of the present invention; and FIG. 7C is a schematic illustration of a cross sectional view of a system for enema purposes, inflated when outside a patient for demonstration purposes, in accordance with an embodiment of the present invention;

FIG. 8 is a schematic illustration of an external object, such as a camera or a detachable capsule, inserted through a tube in a lumen, in accordance with an embodiment of the present invention;

FIG. 9 is a schematic illustration of an object, such as a camera or a detachable capsule, attached to a feed tube extended through a lumen, in accordance with an embodiment of the present invention;

FIG. 10 is a schematic illustration of a lumen into which a 3D camera is introduced according to the present invention;

FIG. 11 is a schematic illustration of a lumen into which a contrast agent is introduced, according to embodiments of the invention; and FIGS. 12 and 13 are schematic illustrations of a device attached to a piston inside a feed-tube.

In all the figures similar reference numerals identify similar parts.

DETAILED DESCRIPTION OF PREFERRED EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

The present invention relates to an apparatus and method for extending a tube through a lumen or other pipe under pressure from a source of fluid flowing through the tube.

The tube may carry only fluid, for example, cleansing fluid or medications, or may carry a device to be delivered to a location inside the lumen or pipe, such as a camera, or any other substances or objects, such as pills, powder, radiation sources, etc.

This is accomplished by providing a tube having a folded portion inside an unfolded portion of the tube, where the fluid flowing into the unfolded portion causes the unfolded portion to unfold and extend out of the unfolded portion.

The present invention provides an endoscopic apparatus reversibly insertable into a curved lumen of a patient, comprising:

a. a flexible sleeve characterized by a proximal end and a distal end; the distal end of the flexible sleeve comprising:
 i. a flexible folded sleeve part comprising at least a portion of the flexible sleeve in a compact and folded arrangement, such that a compact and folded sleeve portion is enclosed within the folded sleeve part; the compact and folded sleeve portion is adapted to unfold and evert at least a portion of the compact and folded sleeve portion, as the same is advanced (i.e., propelled forward) within the curved lumen of a patient; the folded sleeve part is characterized by a predetermined length $L_{fold}$;
 ii. an unfolded sleeve portion in communication with the compact folded sleeve part; the unfolded sleeve portion characterized by a length $L_{unfold}$; $L_{unfold}$ increases as at least a portion of the compact and folded sleeve portion unfolds and everts;

wherein the compact and folded sleeve portion is enclosed and within the folded sleeve part such that a single topologically cylindrical sleeve is provided;

further wherein the enclosing of the compact and folded sleeve portion within the folded sleeve part is provided such that the flexible folded sleeve part advances with the curved lumen when at least a portion of the compact and folded sleeve portion unfolds and everts; further wherein the eversion is provided so as to increase the unfolded sleeve portion length $L_{unfold}$ and such that the flexible folded sleeve part self-navigates within the curved lumen.

The term "about" refers hereinafter to a range of 25% below or above the referred value.

One of the main obstacles left unanswered by the prior art is the fact that the colon is a highly curved lumen; thus, high friction forces exists between any object traveling through the colon and the colon itself. Such friction forces can eventually prevent the object from navigating through the colon.

The present invention overcome such friction by maintaining a substantially constant length to the flexible folded sleeve part (i.e., $L_{fold}$) when fluid is introduced into the folded sleeve part so as to evert and unfold at least a portion of the compact folded portion as the same advances within the colon. Furthermore, the endoscopic apparatus of the present invention maintains $L_{unfold}$ substantially greater than $L_{fold}$, such that the longitudinal shearing forces (i.e., the friction forces) between (a) at least one selected from a group consisting of (i) the folded sleeve part, (ii) the unfolded sleeve portion; and (iii) any combination thereof; and (b) the curved lumen is mitigated so as to enable advancement of the folded sleeve part within the curved lumen.

Yet more, the endoscopic apparatus of the present invention maintains the flexible folded sleeve part and the compact and folded sleeve portion encased within the same in the compact and folded arrangement by ensuring that the forces required to disassemble the compact and folded arrangement are substantially greater than the internal longitudinal shearing forces (i.e., the friction forces) between the flexible folded sleeve part and the compact and folded sleeve portion.

Figure 1B:
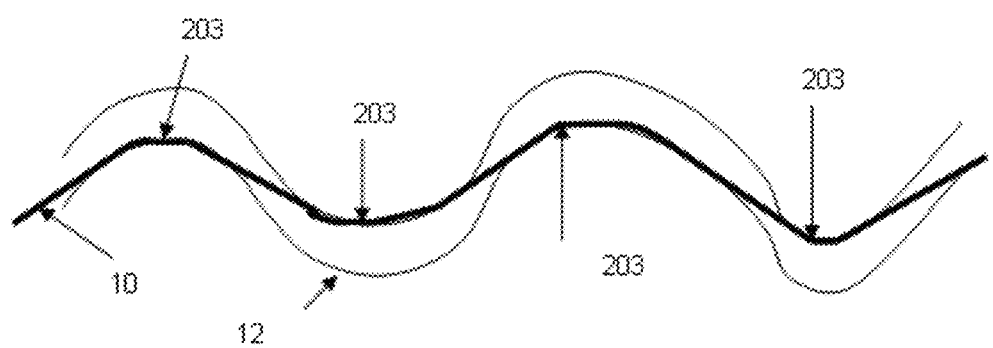
Figure 1A:
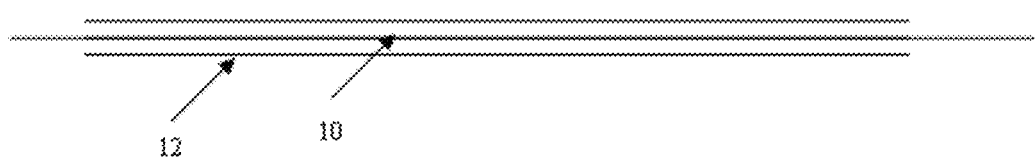

FIGS. 1A and 1B illustrate the longitudinal shearing forces (i.e., the friction forces).

Reference is now made to FIG. 1A which illustrates the friction forces in a straight lumen 12 between the lumen and an object (namely a flexible sleeve) 10. As can be seen in the figure, in a straight lumen practically no friction forces are present. Thus, any object will be able to freely steer through the lumen.

Reference is now made to FIG. 1B which illustrates the friction forces in a curved lumen 12 (e.g. the colon) between the lumen and an object (namely a flexible sleeve) 10. As can be seen in the figure, in a curved lumen there exist many points of friction 203 between the object 10 and the lumen 12.

As mentioned above, one of the main objects of the present invention is to provide an apparatus which will overcome the friction forces issues (by eliminating the same, as will be described hereinafter) and will enable the free navigation of the apparatus throughout the colon.

It should be further emphasized that the fact that the compact and folded sleeve portion is enclosed and within said folded sleeve part so as to provide a single topologically cylindrical sleeve is highly important to the minimization and elimination of the friction forces.

Since the folded sleeve part is highly flexible, the same requires no navigation means for navigating the same through the colon (unlike prior art, which in fact requires navigation means in order to steer through the colon, see e.g., U.S. Pat. No. 7,364,588).

The fact that a steering means (navigation means) is unnecessary means that the endoscopic apparatus of the present invention has small dimensions and maintains its high flexibility.

Figure 1C:
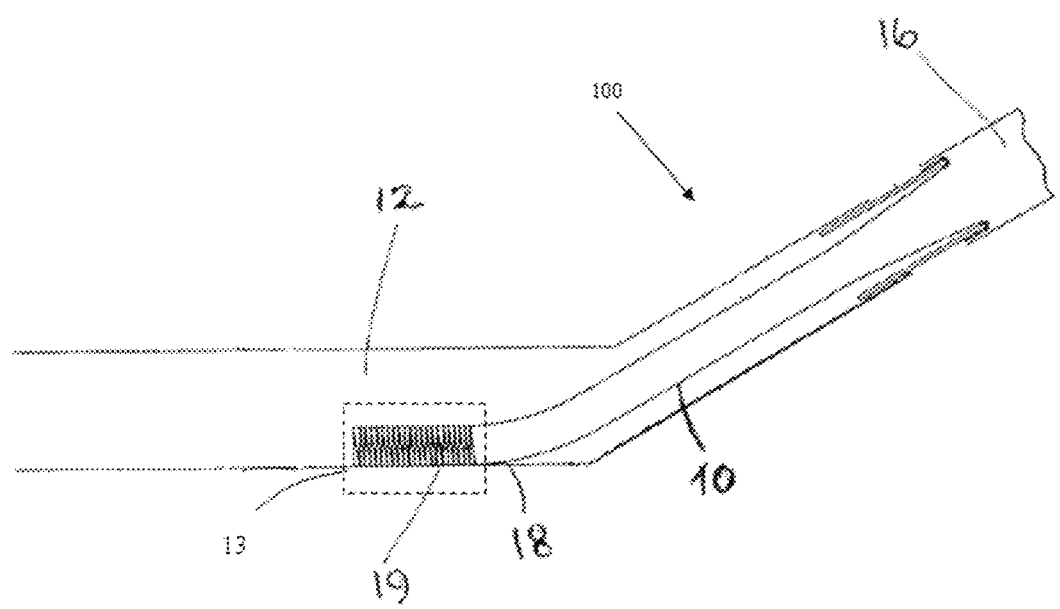

Referring now to FIG. 1C, which provides a schematic illustration of an endoscopic apparatus 100 which comprises a flexible sleeve 10, constructed and operative in accordance with the present invention, partially inserted through a lumen 12 (i.e., the colon).

The endoscopic apparatus 100, and more precisely the flexible sleeve 10, is originally folded inside itself. The flexible sleeve 10 comprises:
 i. a flexible folded sleeve part (13) comprising at least a portion of said flexible sleeve in a compact and folded arrangement, such that a compact and folded sleeve portion 19 is enclosed within said folded sleeve part 13. The compact and folded sleeve portion 19 is adapted to unfold and evert at least a portion of the compact and folded sleeve portion 19, as the same is advanced (i.e., propelled forward) within lumen 12.
 ii. an unfolded sleeve portion 18 in communication with the compact folded sleeve portion 19. The unfolded sleeve portion is characterized by a length $L_{unfold}$.

$L_{unfold}$ increases as at least a portion of the compact and folded sleeve portion unfolds and everts.

The endoscopic apparatus 100 is coupled to a source of fluid 16. When it is desired to extend and to evert at least a portion of the compact and folded sleeve portion 19, for example, within a pipe or lumen 12, fluid from fluid source 16 is permitted to enter the unfolded end 18 of flexible sleeve 10 and to reach the flexible folded sleeve part 13 (or folded portion 19).

In preferred embodiments of the present invention, the endoscopic apparatus 100 is advanced through the lower gastrointestinal tract of a patient by inflation of a flexible sleeve (namely, the compact and folded sleeve portion 19 enclosed within the flexible folded sleeve part 13).

As will be described hereinafter, one end of the sleeve is anchored, typically at or adjacent to the patient's anus.

As the compact and folded sleeve portion 19 is inflated, preferably using a pressurized gas or liquid, the flexible sleeve 10 is propelled forward, and at least a portion of the compact and folded sleeve portion 19 is fed out (i.e., everts) gradually from the flexible folded sleeve part 13 to the unfolded sleeve portion 18.

The portion of the sleeve that is inflated expands radially outward and remains substantially stationary relative to the intestinal wall.

As will be described hereinafter, inflating the flexible sleeve advances the same through the colon, causing the sleeve (i.e., the compact and folded sleeve portion 19) to unfold from the inside out. Thus, an external portion of the sleeve opens out, while the rest of flexible sleeve (namely, the unfolded sleeve portion) stays stationary. This configuration ensures that unfolded sleeve portion 18 maintains stationary (and substantially does not move from its position); thus eliminating friction between the same and the colon's wall. Such elimination of friction ensures that the procedure will be as harmless and painless as possible.

It should be noted that the fluid used to inflate and evert the flexible sleeve can be any fluid which, in the art, is introduced into the body lumen of interest. The fluid can be a liquid or gas or any combination thereof. Non-limiting examples of such fluids are saline, water, washing liquid, sodium phosphate, baking soda, barium compounds, mineral oil, glycerin, laxatives, medicaments, air, nitrogen, oxygen, $CO_2$, xenon and any combination thereof.

As will be described hereinafter, in some preferred embodiments of the present invention, the endoscopic apparatus may additionally comprise instruments for examination, diagnosis and treatment.

According to one embodiment of the present invention, the instruments will be introduced into the flexible sleeve before the same has fully inflated. According to other embodiments, the instruments will be introduced into the flexible sleeve after the same has fully inflated.

Preferably, the instruments include an imaging device, most preferably a miniature video camera and light source, as are known in the art, which are used to capture endoscopic images.

Means for operating the instruments and receiving data therefrom comprise wires, fiber-optic lines, or tubes which are coupled to the instruments and extend to an operator or to equipment outside of the patient, the operator or equipment operating the instruments and receiving data therefrom. The wires, line or tubes may pass through the sleeve.

In preferred embodiments of the present invention, advancing the flexible sleeve through the gastrointestinal tract by means of inflating the same reduces and even eliminates the necessity of applying mechanical force at a proximal end (i.e., outside the patient's body), as is required using conventional endoscopes.

The following disclosure provides better details of the endoscopic apparatus and most preferably of the flexible sleeve.

As described in detail hereinbelow, flexible sleeve 10 is folded inside itself in such a way that, as fluid gradually flows therethrough, folded portion 19 gradually unfolds outwards (i.e., everts) from the folded portion of the tube 19, and becomes an extension of the already unfolded portion 18, thus extending the unfolded portion lengthwise (and increasing $L_{unfold}$).

According to one embodiment of the present invention, the flexible sleeve 10 is formed of material of sufficient strength and flexibility that it extends as the flexible folded sleeve part 19 of the flexible sleeve 10 unfolds, without substantially changing its diameter.

In preferred embodiments of the present invention, the diameter of the flexible sleeve is substantially the same as the diameter of the lumen. As the flexible sleeve is being filled with fluid, as each portion of the flexible sleeve everts from its folded position, the same unfolds radially until it is fully expanded radially, in which condition it is adjacent to a portion of the lumen wall and is in contact with or nearly in contact with that portion of the lumen wall. Once radially expanded, it does not move longitudinally along the lumen. It will remain adjacent to or in contact with the same portion of lumen wall during the entire remainder of the procedure, until the entire flexible sleeve is deflated and removed from the lumen.

Longitudinal movement along the lumen by the flexible sleeve is substantially entirely eliminated because, as the folded sleeve portion everts, it unfolds in such a manner that, as described hereinbelow, it expands from the folded condition to the inflated condition already "in position", radially adjacent to the same portion of lumen wall as it will be adjacent to when the flexible sleeve is fully everted. There is no need for any expanded portion of the flexible sleeve to move longitudinally in the lumen in order to reach its longitudinal position when fully expanded—it initially expands in just that position.

The advantages of initially radially expanding the flexible sleeve into its final longitudinal position include minimizing the pain and discomfort suffered by the patient, as there is no need to force any object to slide along the walls of the body lumen. Another advantage is that the content of the lumen are gently pushed to the side of the lumen and are not forced distally in the lumen. When the lumen is the colon, this greatly increases the hygiene of the procedure—the bacteria-laden contents of the parts of the colon nearest the rectum are not forced inward towards or into the intestines; as is well known in the art, forcing colon contents into the intestines can cause infections.

Figure 2A:
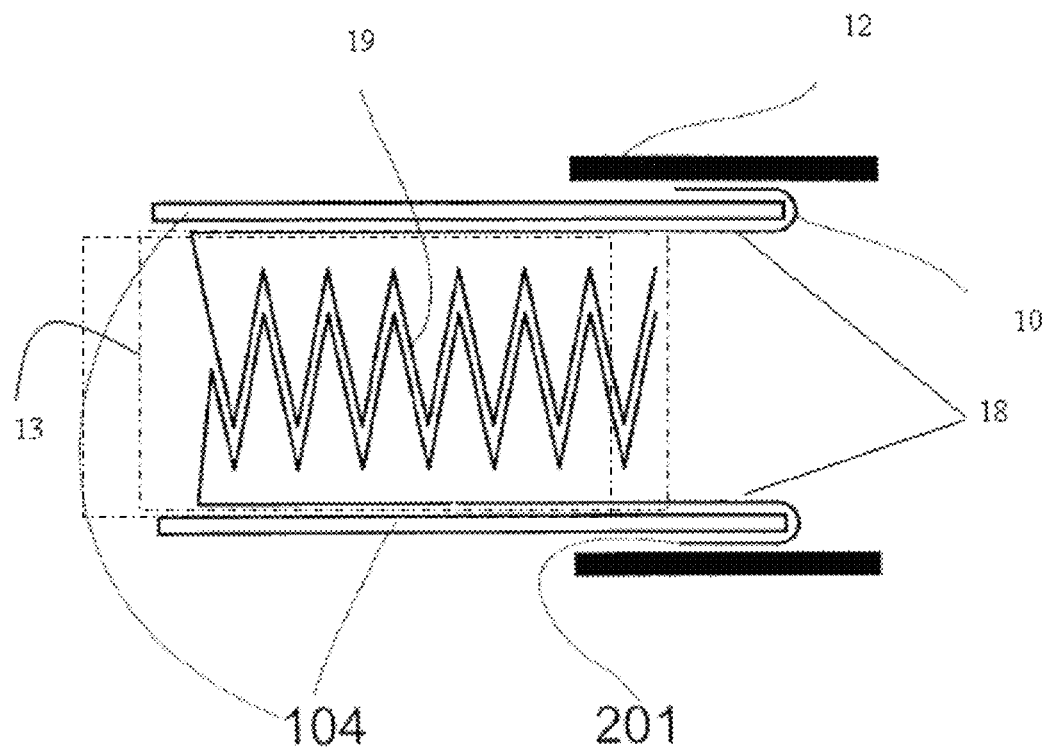
Figure 2B:
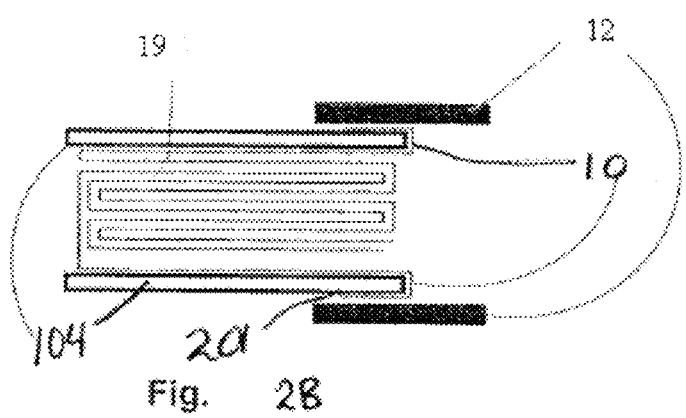
Figure 2C:
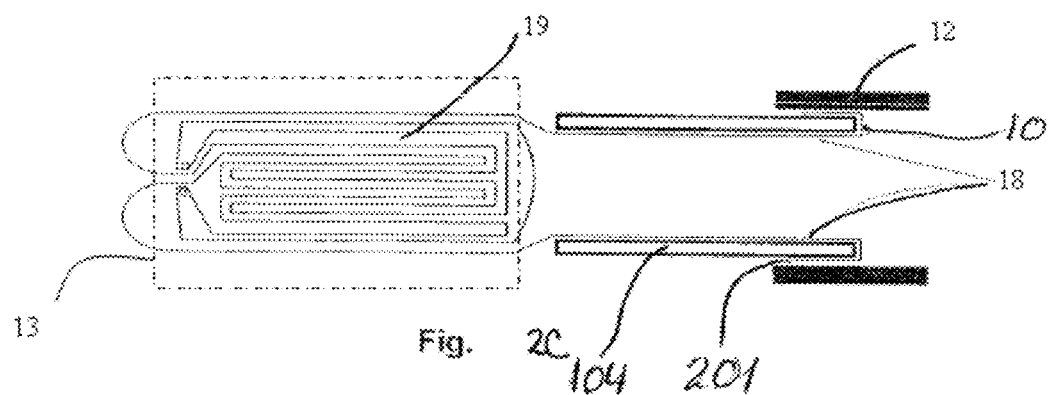

FIGS. 2A, 2B and 2C schematically show three examples of possible packing geometries of the compact and folded sleeve portion 19 enclosed within the flexible folded sleeve part 13 before the same is inflated and everts.

In the introduction of flexible sleeve 10 into a lumen 12 the proximal end portion 201 of flexible sleeve 10 is folded over the proximal (right) edge of a container 104. Thus, flexible sleeve 10 starts at its end portion 201, folded over the right edge of container 104, and is aligned along the inner walls of container 104 towards the left end of container 104.

This portion is already unfolded and is indicated as unfolded part 18 of flexible sleeve 10.

As can be seen in FIGS. 2A, 2B and 2C, folded (packed) part 19 of the flexible sleeve 10 is disposed inside the flexible folded sleeve part 13 of flexible sleeve 10.

It should be emphasized that FIG. 2A also schematically illustrates an accordion folding arrangement of the compact and folded sleeve portion 19.

As can be seen in FIG. 2C, at least a portion of the compact and folded sleeve portion 19 has everted and unfolded from the flexible folded sleeve part 13 to increase the length of the unfolded sleeve portion 18.

There are alternatives to using a container 104 for the introduction of the flexible sleeve 10 into a lumen. One alternative is a semi-rigid tube that looks and feels very much like a straw commonly used for drinking from a cup.

Figure 2D:
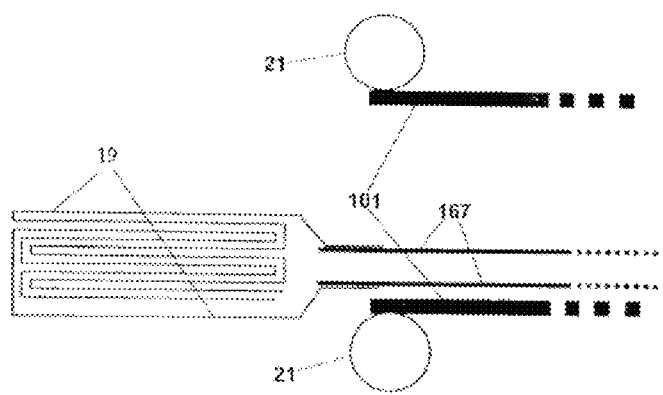

As shown in FIG. 2D, straw-like tube 167 carries the flexible sleeve 10 at its distal (left) end, so that the same can be inflated through straw-like tube 167. Where is it desired to drain the fluid, during extension or once the flexible sleeve has been fully extended, the flexible sleeve can be inserted into the lumen through a drainage channel 101 disposed in the lumen.

Straw-like tube 167 is introduced into drainage channel 101 and is pushed further through channel 101 until straw-like tube 167 sticks out of the distal (left) end of channel 101, as is seen in FIG. 2D.

Preferably, straw-like tube 167 is thinner than the unfolded sleeve portion 18 of the flexible sleeve 10.

This difference in width leaves more room for drainage through drainage channel 101 compared to the situation in which unfolded sleeve portion 18 of flexible sleeve 10 is disposed inside drainage channel 101.

It should be pointed out that the broken lines indicate that these lines continue beyond the frame of the drawing.

Figure 2E:
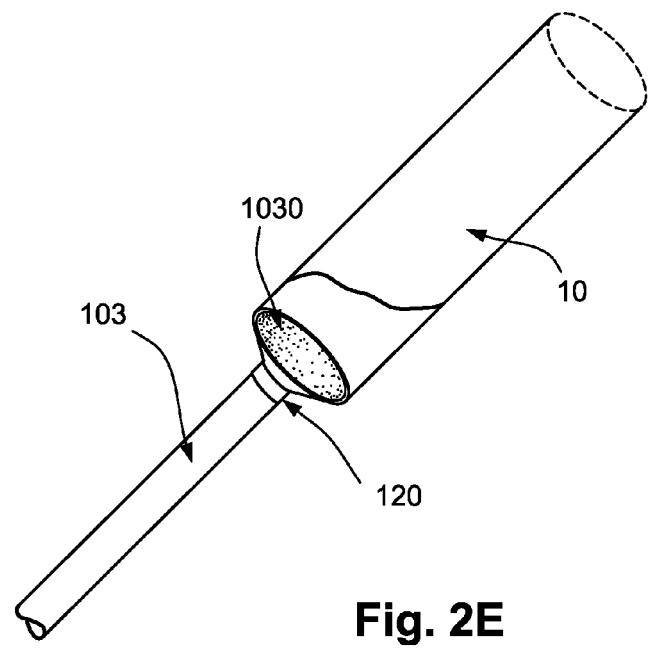

FIG. 2E shows a schematic illustration of an embodiment of a feed tube, comprising a delivery tube 103 linked with a flexible sleeve 10, showing the distal end of the delivery tube 103 and the proximal end of the flexible sleeve 10. The delivery tube is adapted to ease insertion of the folded flexible sleeve at the beginning of a procedure, to provide a means for coupling a fluid container to the flexible sleeve 10 so that fluid can be introduced into the folded sleeve part so as to evert and unfold at least a portion of the compact folded portion as the same advances within the colon, to ensure retention of the flexible sleeve during the procedure, and to ease removal of the flexible sleeve at the end of the procedure. Fluid can be drained from the flexible sleeve via the delivery tube, or the delivery tube can be removed from the flexible sleeve, which can then be connected to a wider drainage channel.

The delivery tube is adapted to sit, in use, partly within the lumen and partly outside the lumen In this embodiment, the delivery tube 103 is of semi-rigid material. It is substantially cylindrical, with a flange 1030 at the distal end, where the flange 1030 is adapted to help retain the flexible sleeve in position relative to the delivery tube during use. In this embodiment, the flexible sleeve 10 is removably linked to the delivery tube 103 by a removable retainer such as, but not limited to, an elastic band, a clip, a tape, a ribbon or any other means known in the art of removably retaining a flexible material juxtaposed to a semi-rigid one.

The flange 1030 is wider at its distal end than at its proximal end, with the diameter of the flange at its distal end being in the range of approximately 2 times as wide as its diameter at its proximal end to approximately 5 times as wide at its distal end than at its proximal end.

The flange can be any convenient shape, for non-limiting example, it can be substantially conical (e.g., as illustrated in FIG. 2E-1), forming a frustum of a cone; substantially spherical (e.g., as illustrated in FIG. 2E-2), forming a portion of a sphere; substantially ellipsoidal (e.g., as illustrated in FIG. 2E-3), forming a portion of an ellipsoid; substantially hyperbolic (e.g., as illustrated in FIG. 2E-4), forming a portion of a hypeboloid, and any combination thereof. In preferred embodiments, as shown in FIG. 2E, the outer surface is smooth; in other embodiments it is rippled or wavy.

In use, flexible sleeve 10, in a folded condition, and delivery tube 103 are inserted in the lumen. The delivery tube is connected to a source of fluid and gently inflated, unfolding and everting along the lumen as described herein. Delivery tube 103 will remain partly within and partly outside the proximal end of the lumen. At least one anchor can be coupled to the delivery tube to ensure that neither the delivery tube nor the flexible sleeve moves laterally relative to the lumen. In preferred embodiments, the anchors are adjacent to the proximal end of the lumen and can be within the lumen or outside the proximal end of the lumen. The anchor or anchors can be any means known in the art of anchoring medical tubes in position relative to a body lumen. A non-limiting example is the inflatable balloon described hereinbelow.

For example, for a colonoscopy, the lumen is the colon and its proximal end, the rectum. The insertion point is the anus and the anchor or anchors would be placed within the rectum, adjacent to the anus, or outside the rectum and adjacent to the anus.

Figure 2F:
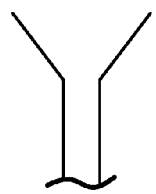
Figure 2F:
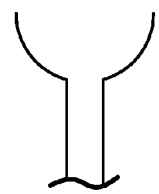
Figure 2F:
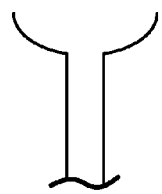
Figure 2F:
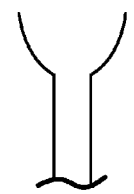
Figure 2F:
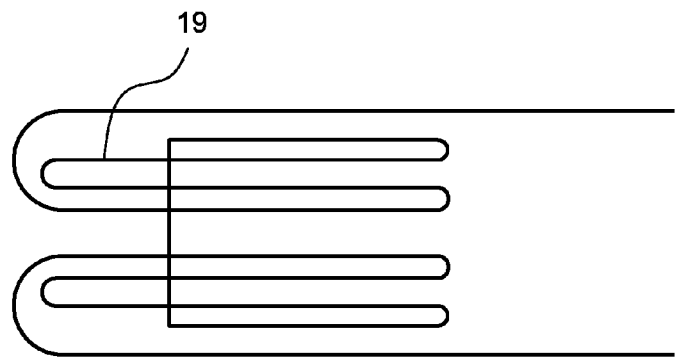

FIG. 2F schematically illustrates a telescopic structure arrangement of the compact and folded sleeve portion 19.

FIG. 2G schematically illustrates a cross section of a spiral-like structure arrangement of the compact and folded sleeve portion 19, in which the compact and folded sleeve portion 19 is rolled up.

FIGS. 2H, 2I, 2J and 2K schematically illustrate a method of assembling the compact and folded sleeve portion of a flexible folded sleeve part where the compact portion has spiral-like structure. In FIG. 2H, a portion of the flexible sleeve has been rolled into a spiral-like structure, as shown in FIG. 2G. In FIG. 2H, the process of inverting the flexible sleeve—turning it inside out like a sock—has been started, with the inverted portion shown at the left. The straight arrow (210) indicates the direction of rolling to create the spiral-like structure. In FIGS. 2H and 2I, the axis of rotation of the spiral-like structure is perpendicular to the longitudinal axis of the flexible sleeve.

In order to fit the spiral-like structure inside the inverted flexible sleeve, its axis of rotation must be rotated by 90° so that the axis of rotation is parallel to the longitudinal axis of the flexible sleeve. This 90° rotation is indicated by the curved arrow 220 in FIG. 2I. FIG. 2J shows an intermediate stage of assembly. The structure has been rotated by 90° so that it fits within the flexible sleeve, at a point where the inverting sleeve partly covers the spiral-like structure.

FIG. 2K shows the flexible folded sleeve part fully assembled; the spiral-like structure has been drawn fully through the flexible sleeve to form a compact and folded sleeve portion at the distal (left) end of the flexible sleeve, while the open, proximal end of flexible sleeve is at the right.

FIGS. 2L, 2M and 2N schematically illustrates, in cross-section, a method of assembling the compact and folded sleeve portion of a flexible folded sleeve part where the compact portion has zigzag structure. In FIG. 2L, the distal end of the flexible sleeve has been folded into a zigzag structure 230 on the right in the figure. The first inversion step is indicated by the arrows 240 at the proximal (left) end of the figure. The flexible sleeve is turned towards the inside, and the flexible sleeve is drawn through the inside of the zigzag compact folded sleeve portion. In practice, a hollow tube or other hollow device (not shown) would be used to support the zigzag compact folded sleeve portion during this first inversion step; the zigzag compact folded sleeve portion would be outside of the hollow support, while the inverting portion of the flexible sleeve would pass through the lumen of the support.

After the flexible sleeve has been fully drawn through the zigzag compact folded sleeve portion, a second inversion process is carried out, as shown in FIG. 2M. In FIG. 2M, the flexible sleeve passes through the lumen of the zigzag compact folded sleeve portion (at the left). On the right, the proximal end of the flexible sleeve is inverted (arrows 250) so as to pass over the outside of the zigzag compact folded sleeve portion. In practice, a second hollow tube or other hollow device (not shown) would be used to surround the zigzag compact folded sleeve portion during this second inversion step; the zigzag compact folded sleeve portion would be inside the lumen of the hollow support, while the inverting portion of the flexible sleeve would pass over the outside of the support. In both cases, the support would be removed after the inversion is completed.

FIG. 2N shows the flexible folded sleeve part fully assembled; the flexible sleeve has been drawn fully through and fully over the zigzag compact folded sleeve portion at the distal (right) end of the flexible sleeve, while the open, proximal end of flexible sleeve is at the right.

Figure 3A:
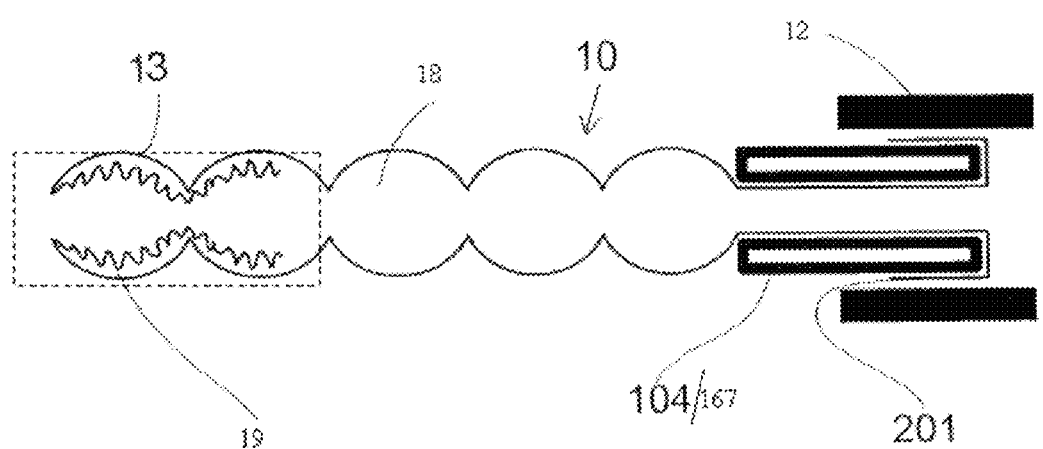
Figure 3B:
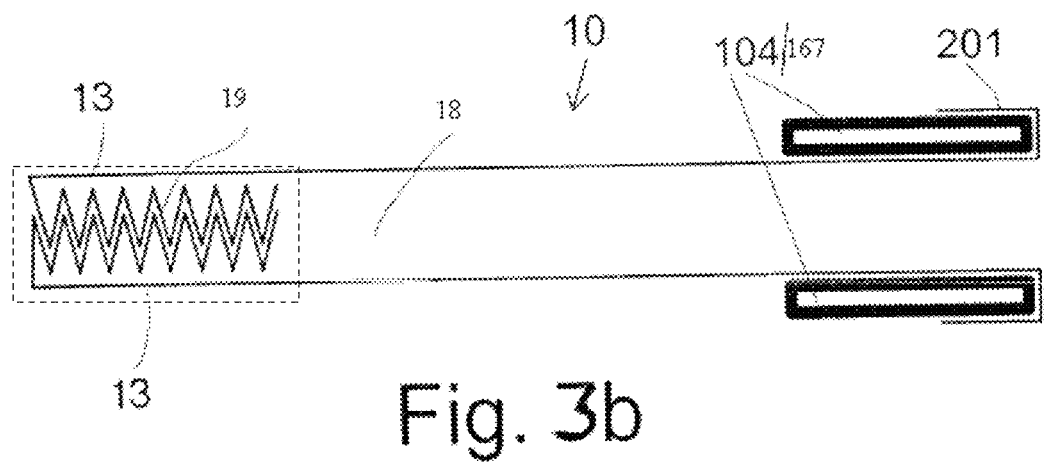

FIG. 3B schematically illustrates a zigzag structure of packed (folded) part (i.e., the flexible folded sleeve part) 13 of the flexible sleeve 10 unfolding during the process of inflation of the same by fluid from the fluid source (not shown), as at least a portion of the pact and folded sleeve portion 19 everts and thus advances further and further to the left (thought the colon 12).

The leftmost fold of folded part 19, inside the flexible folded sleeve part 13, everts (inverts) over the leftmost edge of the flexible folded sleeve part 13 of the flexible sleeve 10, turning inside-out.

As it everts and unfolds, it gets inflated and becomes an additional segment of unfolded part (i.e., the unfolded sleeve portion) 18 of the flexible sleeve 10.

When fluids (e.g., liquid or gas) flows into the flexible sleeve and to the flexible folded sleeve part 13, the leftward portion of the flexible folded sleeve part 13 'pulls' and forces the compact and folded sleeve portion 19 (encased within the same) to the left accordingly (so as to evert and unfold).

This is performed due to the fact that the two parts, compact and folded sleeve portion 19 and the flexible folded sleeve part 13, represent topologically a single soft topologically cylindrical sleeve forming the flexible sleeve.

In other words, the compact and folded sleeve portion 19 is enclosed within the folded sleeve part 13, such that both create a single flexible topologically cylindrical sleeve 10.

In further extension of the flexible sleeve 10 (namely, the folded sleeve portion 19) leftwards (as the same advances within the colon), this unfolding step (of a single fold) is essentially repeated again and again, sequentially, as the flexible sleeve 10 keeps turning inside out, like a sock.

While cylindrical in its topology, flexible sleeve 10 does not necessarily have to be exactly cylindrical in shape.

FIG. 3A shows a non-cylindrical shape option for flexible sleeve 10.

In FIG. 3A, at least a part of flexible folded sleeve part 13 of the flexible sleeve 10 has a cross-section that is quasi-periodically variable along the length of the sleeve.

More specifically, that part of flexible sleeve 10 comprises a plurality of bulging (widened) sections separated by, and thus alternating with, narrowed necks, in a sausage-chain (bead-string) manner. Both the period and the width of the sections and necks may vary along the sleeve.

FIG. 3A also illustrates the compact and folded sleeve portion 19 encased within the flexible folded sleeve part 13 of the flexible sleeve 10.

Compact and folded sleeve portion 19 is illustrated as a concentric zigzag structure of variable width inside the flexible folded sleeve part 13 of the flexible sleeve 10.

As an advantage, compared to cylindrical sleeve 10 of FIG. 3B, the sausage-chain (bead-string) structure of the flexible sleeve 10, shown in FIG. 3A, improves the flexibility and mobility of the same during its extension through lumen 12 as the flexible sleeve 10 is being inflated.

Thus, the sausage-chain shape eases the extension of the flexible sleeve 10 into the lumen 12 that is not straight, for example, a curling colon. In addition, compared to the cylindrical shape of the flexible sleeve 10, a bead-string (sausage-chain) shape of the same reduces the chances of tissue irritation caused by sharp corners at the kinks formed when cylindrical sleeve bends.

As an illustration of both structure and process, FIG. 3A schematically shows also a part of the sausage-chain shaped structure that is not yet unfolded.

FIG. 3A thus illustrates the transition from folded to unfolded state (when at least a compact and folded sleeve portion 19 everts).

Packed (folded) part 19 unfolds (everts) during the process of inflation of flexible sleeve 10, as the same extends further and further within the colon.

A single step of this inflation process occurs as follows:

The leftmost fold of compact and folded sleeve portion (i.e., the folded part) 19, inside the flexible folded sleeve part 13, everts (inverts) over the leftmost edge of the flexible folded sleeve part 13, unfolds, and inflates (i.e., fills with fluid) to become the rounded leftmost bead of the chain of beads of unfolded sleeve portion 18 of the flexible sleeve 10, shown in FIG. 3A.

In further extension, this unfolding step (of a single fold) is essentially repeated again and again sequentially, as the compact and folded sleeve portion 19 keeps turning inside out, like a sock.

FIG. 3B illustrates the same but in a zig-zag folding arrangement of the compact and folded sleeve portion 19 within the flexible folded sleeve part 13.

Preferably, the material of which the flexible sleeve 10 is made is not stretchable significantly at pressures applied during its inflation. This material typically may have a texture similar to that of common sandwich bags. In this way, the flexible sleeve can be unfolded/inflated without increasing substantially in diameter.

At the same time, the flexible sleeve material may have limited stretchability, to help it adapt to the bends and folds in the lumen that it is expanding through. A typical diameter of flexible sleeve 10 for use in colon cleansing is 12 mm. Its length is typically smaller than the length of the colon from the anus to cecum.

FIGS. 3A-3B also illustrates the container 104 or the straw-like tube 167 both of which are coupled to the flexible sleeve 10.

It will be appreciated that the flexible sleeve can be open at its distal end, so that the fluid inflating it can exit from the tube at the end. Alternatively, the distal end of the feed tube can be sealed, as shown in FIG. 4, with one or more exit holes or apertures 108 forming openings in flexible sleeve 10.

Said openings can be scattered along the flexible sleeve's length or located at a predetermined area on the same.

When using apertures 108, the fluid can flow out of the flexible sleeve 10 into the lumen 12 or a drainage channel (not shown).

Alternatively, or in addition, apertures 108 of selected sizes can be formed in certain portions or along the length of flexible sleeve, permitting outflow of fluid at pre-selected distances along the lumen 12.

Different methods of insertion of the tube according to the invention into different lumen for different purposes will now be described, by way of non-limiting example only.

For the purpose of cleansing (washing) the colon, and in other locations where drainage of the inflation fluid is desired, a rigid drainage channel 101, also referred to as insertion tool 101, such as shown in FIG. 6, can be utilized.

Rigid drainage channel 101 is essentially cylindrical, slightly narrowing towards its leading (distal) end, on the left, while widening towards its trailing (proximal) end, on the right.

The flexible sleeve 10 is inserted into the lumen 12 via the drainage channel 101, which serves to support and guide the flexible sleeve.

All along its length, channel 101 is much wider than flexible sleeve, which passes inside channel 101. In other words, the presence of flexible sleeve inside rigid drainage channel 101 leaves a lot of room for drainage, as shown schematically in FIG. 6.

Reference is now made to FIGS. 5A to 5E which schematically illustrate several embodiments of the proposed methods of colon cleansing and the endoscopic apparatus (namely the flexible sleeve), disclosed in the present invention.

In these Figures, a rigid drainage channel 101, as described above, is employed to anchor the flexible sleeve 10 in the rectum 31 of a patient.

A working example of rigid drainage channel 101 has the following dimensions: the length is 14 cm; the outer diameter is 24 mm at the trailing (proximal) end, on the right, tapering down to 20 mm at the leading (distal) end, on the left; the wall thickness is 1.0 to 2.0 mm. Typically, the material of rigid drainage channel 101 is conventional rigid plastic.

According to another embodiment of the present invention, means are provided so as to ease the insertion of the rigid drainage channel 101 into anus 31.

Figure 5A:
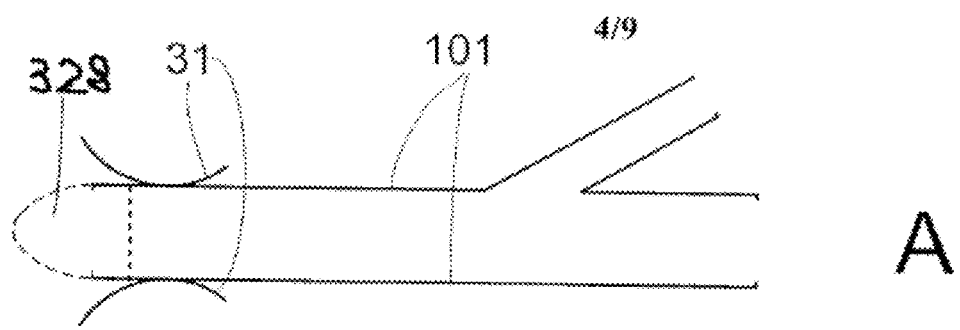

According to this embodiment, a removable cap 328, seen in FIG. 5A, makes the insertion of the rigid drainage channel 101 into anus 31 smoother.

The removable cap 328 'covers' the leading edge of rigid channel 101 and creates an oval shape to the leading edge of rigid channel 101.

One way to make cap 328 is by coating the leading edge of channel 101 with a formable material and letting the material harden.

Alternatively, cap 328 is formed separately from channel 101. For example, cap 328 can be made of ice by filling a cap form (a mold) with water and freezing the same.

Such separately made ice cap 328 is stored frozen and is inserted into the leading end of rigid drainage channel 101 just before usage.

Cap 328 can be made of a material that would melt, soften, dissolve or any combination thereof upon being inserted into anus 31. Preferably, the material of cap 328 is ice. The cap can cover the leading (left) edge of rigid channel 101 either on the inside or on the outside of channel 101, or both. When ice cap 328 covers the edge of rigid channel 101 on the inside, the ice fills channel 101 to the depth of a few millimeters from the leading (left) edge, as in FIG. 5A.

At the start of the procedure, rigid channel 101 is inserted into anus 31 with ice cap 328 sitting on its leading edge.

Figure 5B:
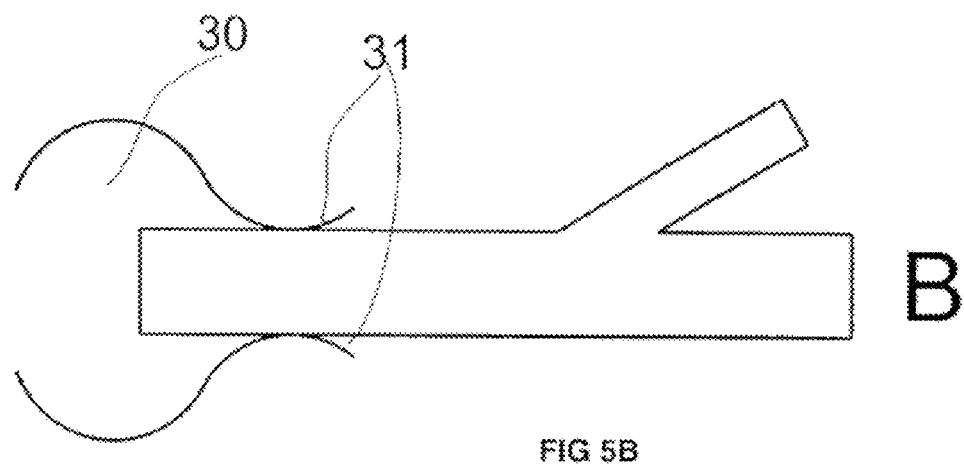

Then warm, body temperature, liquid is pumped via rigid channel 101 into the body, from right to left. The warm liquid pushes ice cap 328 out of rigid channel 101, into the body, and melts the ice cap, at least partially, as shown in FIG. 5B.

Another way to smooth the insertion of rigid drainage channel 101 is to provide cap 328 made from a material more durable than ice, for example plastic.

In this case, cap 328 should be removable from its place at the end of channel 101 and then be withdrawn from the body of the patient.

For this purpose, cap 328 may be composed of segments small enough to be pulled back through the rigid drainage channel 101 with a flow of liquid.

According to one embodiment of the present invention, the cap may fall apart as it is pushed out of rigid drainage channel 101 forward, by a flowing liquid in channel 101 for this purpose.

Alternatively, the cap may fall apart manually by pushing a piston, squeezing a bulb syringe, a fleet enema type device, or in a similar way. Then, as the liquid drains back, out of rectum 30 through channel 101, the cap segments float (eventually, as more liquid drains out) with the liquid flow through rigid drainage channel 101 into the sewage.

Figure 5C:
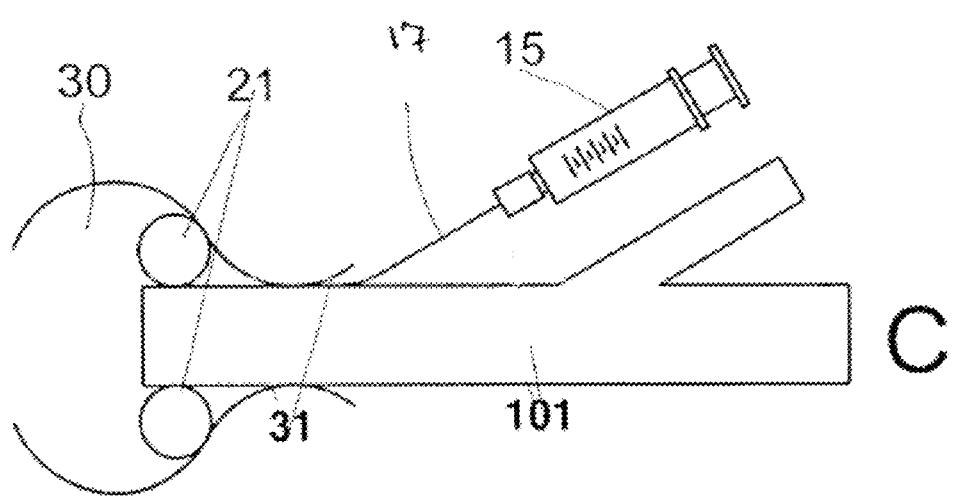

In order to firmly anchor the drainage channel 101 in the anus 31 and prevent leakage of fluid, an inflatable balloon 21 may be inserted inside rectum 30 (see FIG. 5C).

Reference is now made to FIG. 5C, which illustrates such an embodiment. In the figure, the part of rigid drainage channel 101 that is inside the rectum is attached to an inflatable balloon 21. Balloon 21 is inflated inside the rectum by means of an external pump, in order to maintain the drainage channel 101 in its position and to prevent the same from exiting from the anus.

FIG. 5C also illustrates a pumping device 15, such as a syringe, for inflating balloon 21. Pressure-providing tube 17 conducts the inflating liquid or gas from pump device 15 to balloon 21.

The diameter of pressure-providing tube 17 is typically between 0.5 and 2.0 millimeters.

Tube 17 may be fixedly connected, e.g., inflation and deflation tube.

In this way, pump device 15 can inflate the balloon to create the necessary seal at the start of the procedure, and can be used to deflate the balloon 21 at the end of the procedure.

Optionally, a one-way valve (not shown) is installed between pump device 15 and balloon 21 for preventing balloon 21 from deflating prematurely.

Manual opening of such a one-way valve causes balloon 21 to deflate. Inflated balloon 21 together with rigid drainage channel 101 is wider than rigid drainage channel 101 alone, typically by 20-40 mm. In other words, inflated balloon 21 adds 8-32 mm to the diameter of the device, typically maintaining rigid drainage channel 101 in its position and preventing the same from exiting from anus 31.

Figure 5D:
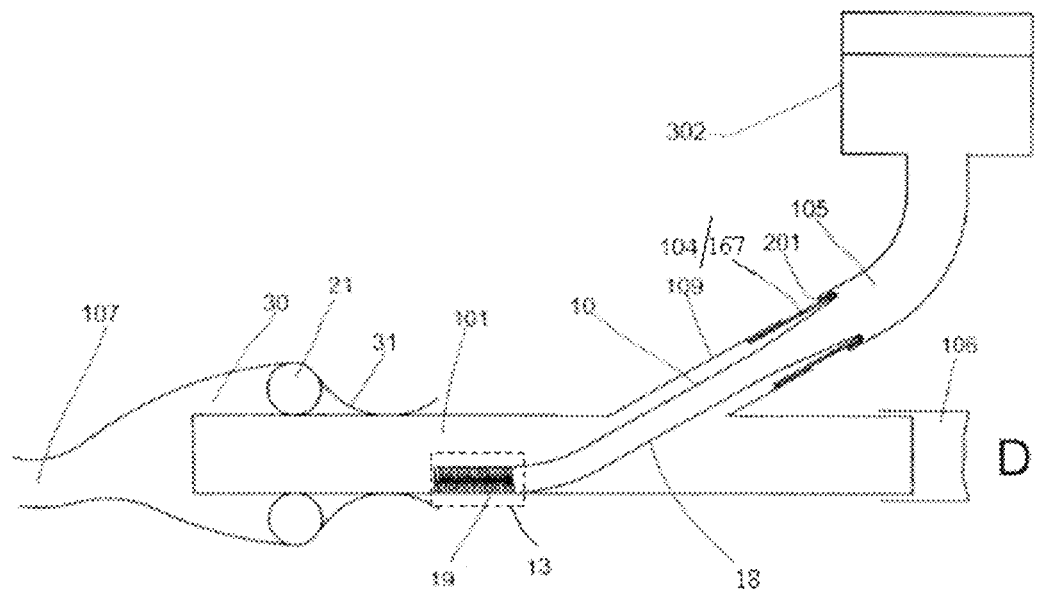
Figure 5E:
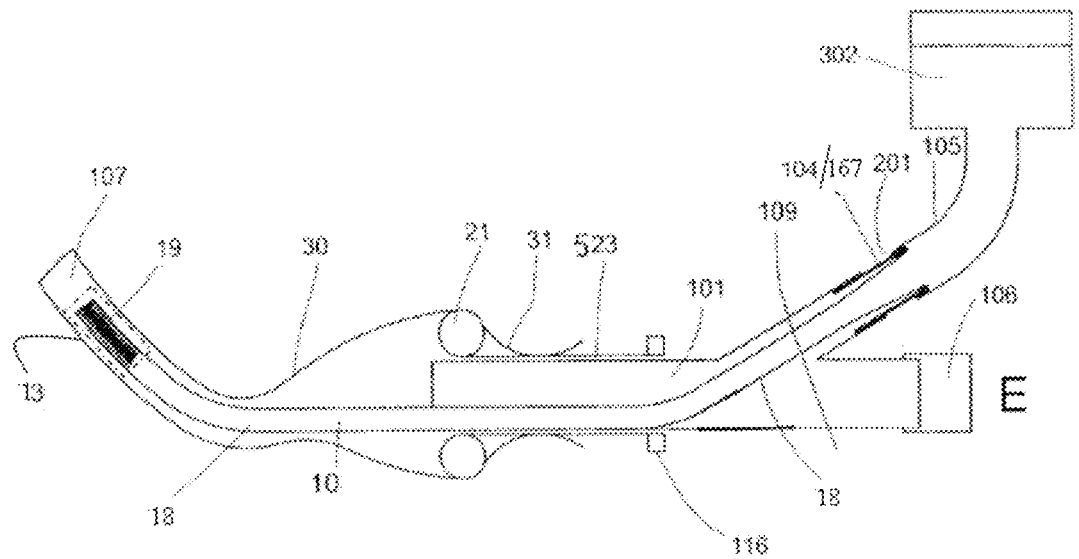

Preferably, balloon 21 is a ring shaped toroid encircling rigid drainage channel 101, as shown in FIGS. 5C and 5E, close to the topologically circular leading (left) edge of channel 101; or in other words, the ring shaped balloon 21 is sized and dimensioned as an inflatable cuff around essentially cylindrical channel 101.

Therefore, when balloon 21 is ring shaped, it can be referred to as inflatable cuff 21.

During the insertion of rigid drainage channel 101 into anal canal 31, the balloon 21 is preferably kept deflated under removable cap 328.

According to another embodiment of the present invention, the ring shaped balloon 21 may be attached to rigid drainage channel 101 by means of sheath 523, seen in FIG. 5E.

Sheath 523 is optionally glued to channel 101 or otherwise affixed to it. Alternatively, sheath 523 may be reversibly attached to channel 101.

Sheath 523 can be either rigid or pliable, depending on the embodiment.

According to another embodiment, the part of drainage channel 101 that is outside of the rectum is attached to another inflated balloon (not shown), adapted to assist in maintaining the drainage channel 101 from moving too far into the rectum.

Before the inflation of the flexible sleeve starts, flexible sleeve 10 is packed into rigid container 104 or straw-like tube 167. Then rigid container 104 or straw-like tube 167 is inserted into rigid feed holder 109 that branches out of rigid drainage channel 101 at a sharp angle backwards, as shown in FIGS. 5D and 5E.

With its inflation, flexible sleeve 10 unfolds and extends out of container 104 (or straw-like tube 167) via rigid feed holder 109 and further via drainage channel 101 into rectum 30 and still further into colon 107, as shown in FIG. 5E.

The inner diameter of rigid feed holder 109 is typically slightly larger, for example by 1.0 or 2.0 mm, than the outer diameter of unfolded sleeve portion 18 of the flexible sleeve 10.

The material of container 104 (or straw-like tube 167) is typically conventional rigid plastic.

Rigid feed holder 109 is typically integrally formed with, or firmly affixed to, drainage channel 101 and is made of the same material.

Liquid for washing the colon is stored in a reservoir 302, as seen in FIG. 5D. A small hose 105 conducts the washing liquid from reservoir 302 down into flexible sleeve 10.

The washing liquid flows down inside small hose 105 under the pressure of its own weight. In other words, the liquid is being pulled by the force of gravity.

Alternatively, a pump (not shown) can be provided, if desired, to pump the fluid from reservoir 302 into flexible sleeve 10.

The flexible sleeve 10 is shown in FIG. 5D to be advancing through drainage tube 101 into rectum 30.

The mechanism of the advance of flexible sleeve 10 within colon 107 is by inflation and unfolding (eversion) of at least a portion of the compact and folded sleeve portion 19 encased within the flexible folded sleeve part 13, as the flexible sleeve 10 is being filled with the washing liquid from reservoir 302.

The inflation pressure may be comparable to pressures used in common enemas and, more generally, is between about 0-1 atm higher than atmospheric pressure.

The inflation of flexible sleeve 10 extends (increases the length of) the unfolded sleeve portion 18 with little change in its width. The increase in the length of unfolded sleeve portion 18 occurs due to the sequential unfolding of a portion of the compact and folded sleeve portion 19 enclosed within the folded sleeve part 13 of flexible sleeve 10 into the unfolded part 18 of the flexible sleeve 10.

Preferably, the sequential unfolding is performed by eversion, in other words by turning inside-out of compact and folded sleeve portion 19 into the unfolded part 18 of the flexible sleeve.

It is essential that folded part 19 will be located inside flexible folded sleeve part 13 of the flexible sleeve 10.

In other words, eversion is like turning a sock inside out.

It will be appreciated that, in this way, the flexible sleeve 10 extends through the colon substantially without friction between the same and the lumen 12 walls.

It is also important to minimize the friction between the flexible folded sleeve part 13, the compact and folded sleeve portion 19, the unfolded sleeve portion 18 and the lumen 12.

This friction arises primarily due to the fact that there are turns in the curling lumen. The friction rises dramatically as there is more contact between flexible folded sleeve part 13, the unfolded sleeve portion 18 and the lumen.

Therefore, it is preferable to minimize this length by making the packing of flexible folded sleeve part 13 as compact as possible.

In other words, good packing should minimize the trailing of folded part 13. For example, it can easily be seen that the packing structure shown in FIG. 2A allows much more trailing as compared to those shown in FIG. 2B and FIG. 2C.

In preferred embodiments of this invention, the packing is maintained compact during the inflation of the feed tube. Specifically, the criterion of good packing is the following: during inflation, the maximal size achieved by folded part 13 should be much smaller than the maximal length of unfolded part 18.

More specifically, according to a preferred embodiment of the present invention, the folded sleeve part 13 is characterized by a predetermined length $L_{fold}$; and the unfolded sleeve portion 18 is characterized by a length $L_{unfold}$. As described above, $L_{unfold}$ increases as at least a portion of the compact and folded sleeve portion 19 unfolds and everts.

According to a preferred embodiment of the present invention, predetermined length $L_{fold}$ remains substantially the same when fluid is introduced into the folded sleeve part 13 so as to evert and unfold at least a portion of the compact folded portion 19 as the same advances within said curved lumen, such that longitudinal shearing forces between (a) at least one selected from a group consisting of (i) the folded sleeve part, (ii) the unfolded sleeve portion, and (iii) any combination thereof; and (b) the curved lumen is mitigated so as to enable advancement of the folded sleeve part within the curved lumen.

In FIG. 5E, flexible sleeve 10 is shown to be advancing via anal canal 31 into colon 107.

In the process of its advance, flexible sleeve 10 is being filled with the washing liquid from reservoir 302 and reaches a length at which an exit hole or holes, such as hole 108, opens in the flexible sleeve.

Then the washing liquid flows out of the exit hole of the flexible sleeve 10 into colon 107 and washes colon 107 by flowing outside of flexible sleeve 10 back towards the drainage channel, in the direction from the cecum to the anus.

The washing liquid is drained out of rectum 30 via rigid drainage channel 101 and further via drainage port 106 through a hose out into sewage system. The washing liquid continues to flow inwards through flexible sleeve 10 in the direction from anus 31 deep into colon 107 and continues to flow back outside feed tube through colon 107 towards the anus, thus washing colon 107.

It will be appreciated that the washing liquid can be arranged to flow out through feed tube into the colon at substantially any location along the colon.

However, the arrangement of the present invention is particularly suited to providing washing liquid substantially to the cecum, thereby providing non-traumatic cleansing of substantially the entire colon, which is not possible with conventional lavage devices, which drive water up into the colon from the anus, so not much water reaches the cecum and which is problematic for bacterial flora preservation.

It will be appreciated that the pumping of the liquid via rigid channel 101 into the body, from right to left can be done in various ways. One way is to supply the liquid via rigid feed holder 109. Another way is to split the passage of liquid via drainage port 106 into two passageways—one for draining out, the other for pumping in. One way valves, clamps, etc. can be used to close one or both passages.

The liquid for pumping in can be supplied from a reservoir 302. If a vigorous flow is needed to be pumped in, the flow can be generated manually by pushing a piston, squeezing a bulb syringe, a fleet enema type device, or in a similar way.

It will be appreciated that a rigid drainage channel is not always required or desired. FIG. 7A illustrates direct insertion of a flexible sleeve 10 via the anus into the rectum, without the benefit of a drainage channel at all.

The container 104 (or straw-like tube 167) of flexible sleeve 10 is coupled via a small hose 105 to a liquid reservoir 302. The flow of liquid from reservoir 302, under the force of gravity, causes the unfolded portion 19 of flexible sleeve 10 to gradually unfold, as described above. Alternatively, as mentioned above, a pump can be used.

FIG. 7B illustrates a pliable (soft) drainage channel 23, which can be used instead of the rigid drainage channel 101 shown in FIG. 5E.

Channel 23 is essentially a soft sleeve and is also referred to as pass sleeve 23.

Like rigid drainage channel 101, pass sleeve 23 is used for draining the washing liquid and feces out of the body. Yet, unlike in rigid drainage channel 101, the drainage via pass sleeve 23 is accomplished, at least in part, by natural motion of the muscles of the rectum and sphincter, and by the natural opening of the anal canal.

Pass sleeve 23 is shown to be attached to inflated toroidal ring-shaped balloon 21 that rims the circular edge of the distal end of channel 23. Ring-shaped balloon 21, also referred to as inflatable cuff 21, is inflated after the same is inserted inside rectum 30 and keeps the leading end of pass sleeve 23 inside rectum 30.

Reference is now made to FIG. 7C, which is a schematic cross sectional view of pass sleeve 23 with attached toroidal ring-shaped balloon 21 when inflated outside of a patient, for demonstration purposes. For the purpose of drain waste disposal, proximal end 24 of pass sleeve 23 can be connected to a container (not shown) or a sewage hose.

For enema purposes, the proximal end 24 of pass sleeve 23 can be connected to a bag filled with a liquid. For both drain disposal and enema purposes, together, both connections can be made to the same proximal end 24 of pass sleeve 23. The two hoses can be closed by clamping them, usually done alternatively, one at a time.

Either way, the connection of proximal end 24 of pass sleeve 23 to downstream drain vessels is implemented by means of a conventional plumbing connector 25.

Toroidal ring-shaped balloon 21, when fully inflated, preferably has an inner diameter of between 30 and 80 millimeters.

Its outer diameter is larger, typically by 5 to 40 millimeters, than its inner diameter.

As in FIG. 7C, the diameter of pass sleeve 23 is typically close to the inner diameter of toroidal balloon 21 and, thus, ranges typically between 30 and 80 millimeters. The diameter of pass sleeve 23 does not have to be uniform along the sleeve, but rather can be designed to vary, depending on various requirements.

Therefore, the cylindrical shape of pass sleeve 23 in FIG. 7C is only a non-limiting example. The inflated ring of toroidal balloon 21 does not have to be exactly circular, and neither do any of its cross sections. Toroidal ring-shaped balloon 21 can be inflated with liquid to less than its full volume. Such partial inflation leaves balloon 21 soft enough to adapt itself to the shape of the body canal, such as rectum, in which it is located. This way, irritation of the canal wall is minimized.

FIG. 7B illustrates the flexible sleeve 10 passing inside pass sleeve 23 into rectum 30.

Later, the flexible sleeve 10 is further extended by inflation deep into the colon. Then, the flexible sleeve 10 conducts the washing liquid into the colon.

To prevent the sphincter from squeezing pass sleeve 23 and, thus, closing the flow of liquid through the flexible sleeve 10 (inside pass sleeve 23), a rigid tube that is wider than the flexible sleeve 10 is inserted into pass sleeve 23 inside the anus. The flexible sleeve 10 is passed inside this rigid tube.

The rigid tube can be made wide enough to serve both for passage of the flexible sleeve 10 into colon 107 and for drainage from the rectum out.

In this dual role, this rigid tube is very much like rigid drainage channel 101. Therefore, this rigid tube is referred to herein using the same term and numeral—rigid drainage channel 101.

In the same procedure, drainage can be carried out via both rigid drainage channel 101 and pass sleeve 23. Pass sleeve 23 is preferable for draining large fecal bodies that may clog rigid drainage channel 101. By contrast, the latter is preferable for liquid drainage, as well as for small and medium size fecal bodies. If a large fecal body clogs rigid drainage channel 101, then a flow of liquid in the reverse direction, towards the rectum, is used to unclog channel 101. If necessary, the unclogging procedure is repeated until the clogging material goes out through pass sleeve 23.

Before the cleansing begins, rigid drainage channel 101 together with inflatable balloon cuff 21 and the leading portion of pass sleeve 23 are inserted into anus 31 with the help of an ice cap or other removable cap, similar to cap 328, described above.

Part of pass sleeve 23 is lined up along the outer surface of rigid drainage channel 101. Vaseline is spread on the outside of this part of pass sleeve 23 for smoother insertion into anus 31.

The materials of the flexible sleeve 10, pass sleeve 23 and toroidal balloon 21 have limited stretchability, particularly under inflation pressures and other forces applied during the procedure.

These materials typically have a texture similar to the texture of common sandwich bags. Non-limiting examples of suitable materials include polyethylene (preferably low density polyethylene), polypropylene, and polyurethane. The materials should be as biocompatible as reasonable and have no or minimal toxic or harmful effects.

The thickness of these sheet materials typically ranges between 10 and 150 micrometers and is preferably about 40 micrometers. The thickness and the nature of the sheet materials of the flexible sleeve 10, pass sleeve 23 and toroidal balloon 21 do not have to be necessarily uniform along the surface and thus, may be heterogeneous thickness. Multiple layered sheets can be used, especially for making balloon 21, where leaks are least desirable.

Methods for producing the flexible sleeve 10, pass sleeve 23 and toroidal balloon 21 may vary. Prefabricated sheets of the material can be purchased wholesale. The sheets can be heated by applying a properly shaped hot wire to make pieces of appropriate shapes. Either then or later, while the appropriate edges of the pieces are heated, they are stitched together, as needed, to form seams. Other common methods of production are by extrusion or dip molding. Preferably, the parts are disposable.

As stated above, the flexible sleeve, according to the present invention, is advanced within the lumen or pipe (e.g., colon) by inflation with a liquid or a gas, can be used for purposes other than cleansing the colon.

According to one embodiment of the invention, as FIG. 8 illustrates, flexible sleeve 10, after being unfolded in the appropriate lumen, can be used as a channel for insertion of an endoscope 135 through flexible sleeve 10 for delivering an object 136 to a desired location inside a patient's body.

Object 136 can be, for example, a camera, a detachable capsule, a source of radiation, such as: light, X-rays, positrons, other radioactivity, etc., or any other object to be delivered thereto.

According to another embodiment, as FIG. 9 illustrates, an unfolded the flexible sleeve 10 can, itself, be used as an endoscope. In this case, the object 149 is attached directly to the flexible sleeve 10 itself, for insertion through the lumen as the flexible sleeve 10 unfolds.

According to another embodiment the object 149 is not attached to the flexible sleeve and is just introduced within the same.

Unfolded the flexible sleeve 10 is shown here to carry object 149 attached at the end of tube 123, although object 149 could, alternatively, be attached at some other point along the length of tube 123. Object 149 can be, for example, a camera, a detachable capsule, a source of radiation, or any other appropriate object.

In FIG. 9, the flexible sleeve 10 is preferably closed at its distal end. By contrast, in FIG. 8, and for washing purposes, flexible sleeve 10 is open, preferably at the very (distal-most) end, for delivering object 149 or the washing liquid, respectively.

According to one embodiment, the diameter of the very (distal-most) end of the flexible sleeve 10 is slightly smaller than the diameter of the main part of flexible sleeve 10 so as to maintain object 149 at the distal end of the same and to prevent the discharge of said object to the colon. Such an embodiment also enables washing of the colon.

According to one embodiment, the object 149 is introduced into the flexible sleeve 10 after the same has been fully extended (fully unfolded) within the colon. According to another embodiment, the object 149 is introduced while the flexible sleeve 10 is not fully extended within the colon.

One specific application of flexible sleeve 10 shown in FIG. 9. In the figure a visual inspection of the colon using a camera located in object 149 is provided.

During the inspection, flexible sleeve 10 is preferably gradually withdrawn from the colon, as in conventional endoscopy. For the latter application, flexible sleeve 10 may include a section at its very end that is wide enough to expand the colon walls outwards for inspection. In other words, this wider section of flexible sleeve 10 spreads the wall out for visual examination of the wall portion sliding off the wide section, as flexible sleeve 10 is gradually withdrawn from the colon. The image seen by the camera can be transmitted wirelessly from object 149 to an appropriate receiver. The inspection can be performed in real time, after a video or still recordings of the images from the camera are made, or any combination thereof.

FIG. 10 schematically shows a plurality of cameras 402 attached to a shaped flexible sleeve 10. The delivery of cameras 402 into colon 107 is by inflation of the flexible sleeve 10, its unfolding and advancing within lumen 107, as described above.

The properties and handling of the flexible sleeve 10 in this embodiment is essentially the same as described above.

After complete inflation of flexible sleeve 10 within lumen 107, the same may be withdrawn. FIG. 10 illustrates the withdrawal of the flexible sleeve 10 through lumen 107.

Balloons 405 and 408 in FIG. 10 are essentially two widened portions of the flexible sleeve 10. Alternatively, they can be coupled to an independent tube, coupled to the flexible sleeve 10.

Alternatively, both balloons can be inserted once the flexible sleeve 10 has already been fully or partially extended (inflated).

Balloon 408 is at the trailing (leftmost) end of the flexible sleeve 10. Balloon 405 is close to balloon 408 along the flexible sleeve 10, at a distance comparable to the characteristic diameter of the balloons, typically several centimeters.

The two balloons, 405 and 408, engage the walls of lumen 107 as the same are inflated. Said inflation are adapted to maintain the walls at an appropriate distance from cameras 402 so as to enable the same to take pictures of the walls. According to one embodiment, six cameras 402 are used, in three pairs.

The fields of view of the cameras are indicated by two diverging punctured lines 409. In each of the three pairs of cameras shown in this example, the two cameras in the pair have overlapping fields of view. The overlap of the two fields of view allows a reconstruction of a three-dimensional (3D) image of the wall of lumen 107 (binocular parallax method).

Alternatively, reconstruction of 3D images can be carried out from data collected from a single camera, rather than two cameras.

For example, the second camera can be replaced with a mirror chain, while the image data are collected alternatively from one point of the chain and another. Yet another option is to reconstruct 3D image from single camera shots taken at different points of the trajectory of its withdrawal along the colon (motion parallax).

Still another option is structured light depth extraction, such as described in U.S. Pat. No. 6,503,195. The image data from one or more cameras can be sent to an outside computer either wirelessly, i.e., via a transmitter, or by wire, such as an electric cord or optical fiber (not shown).

In the example of FIG. 10, each camera 402 carries a simple source of light, such as a LED, for illumination of the lumen wall. An alternative is a source of structured light for depth extraction. Such source is preferably located away from the camera recording the image for depth extraction, yet can be attached to the same surface, such as that of balloons 405 and/or 408. The image data, whether still or video, whether 3D or not, can be viewed in real time or recorded for subsequent viewing. Descriptions of methods of 3D image reconstruction can be found in U.S. Pat. Nos. 6,503,195; 6,798,570; 6,949,069; 6,749,346; 6,563,105; 5,751,341; and 5,673,147.

If the image data are to be recorded for subsequent viewing, the data collection can be performed by a nurse or technician, rather than by a doctor. The doctor's attention can subsequently be focused more fully on viewing, rather than on both viewing images and handling an endoscope at the same time. 3D image viewing can be done using artificial shading, virtual rotation, binocular glasses, light polarization glasses, or any other convenient method of 3D display. Computerized pre-processing of the 3D images can select and flag spots that may need extra attention by the human viewer.

Referring now to FIG. 11, there is shown a schematic illustration of the use of the flexible sleeve 10 for delivery of a contrast agent for medical imaging to colon 107.

In this example, the contrast agent is barium sulfate, also called "barium". Barium is commonly used as a suspension of fine particles in an aqueous solution in the medical imaging technique called "barium enema", a procedure for colon imaging. Other contrast agents, such as water soluble contrast agents, can be used instead of barium. Unlike in a standard barium enema, here in FIG. 11, barium fills only a small portion of colon 107, between balloons 405 and 408.

As described above, balloons 405 and 408 are essentially two widened portions of the flexible sleeve 10. Balloon 408 is shown to be at the trailing (leftmost) end of the flexible sleeve 10.

Balloon 405 is close to balloon 408, typically at a distance of several centimeters.

The delivery of balloons 405 and 408 into colon 107 is by inflation of the flexible sleeve 10; and unfolding and advancing into colon 107, as described above.

After the inflation and advance of the flexible sleeve 10 into colon 107, the same may be withdrawn. FIG. 11 shows the withdrawal of the flexible sleeve 10 through colon 107.

In FIG. 11, barium is shown to fill the colon between balloons 405 and 408. Thus, the segment of the colon filled with barium is well defined and controlled by the location of balloons 405 and 408.

As balloons 405 and 408 are being withdrawn from colon 107 (towards the right), the barium filling 'moves' with the balloons' movement.

During this withdrawal, barium can be spread along the walls of colon 107 behind balloon 408. This coating of the colon's wall 107 with barium is achieved by the sliding motion of balloon 408 along colon wall 107.

Thus, the barium coating of the walls of colon 107 creates a special contrast, similar to that in an "air contrast barium enema". One advantage of the arrangement in FIG. 11 over a conventional "air contrast barium enema" is that, in FIG. 11, the coating of the walls with barium can be controlled by adjusting the size and shape of balloon 408. For example, the smaller balloon 408, the thicker will be the barium coating on the wall behind the balloon, generally.

In conventional "air contrast barium enema", barium is pushed along the colon by pumping gas, such as air, into the colon. Correspondingly, the conventional barium coating formation is less tunable than that in the technique shown in FIG. 11.

In FIG. 11, the contrast agent, such as barium, is delivered via a delivery tube 86 through opening 89 into the colon.

Delivery tube 86 may be attached to the flexible sleeve 10 or the inside of the same.

If tube 86 is coupled to the flexible sleeve 10, during the unfolding of the flexible sleeve 10 within the colon 107, the delivery tube 86 is also unfolded.

It will be appreciated that the device and method of FIG. 11 can be used for procedures and in locations other than colon enema, such as introducing at least one medication.

Similarly, once tube 86 has been unfolded to the desired location, gentle suction can be applied to the same thus, if it is formed of sufficiently strong material, permitting withdrawal of liquids or fluids from various locations inside the lumen.

According to another embodiment of the invention, the unfolded tube 86, itself, can be used to massage a wall of a lumen. In this case, the tube may be of such dimensions that it conforms to the walls of the lumen, or a portion of the lumen can be massaged at one time.

Massage can be provided by moving the flexible sleeve 10 itself; by sending flows of fluid through flexible sleeve 10; or by moving massaging objects, such as inflated balloons, by means of or through the fluid that fills the extended tube.

As described above, according to some embodiments of the invention, a camera or other device for internal inspection or treatment can be inserted to a desired location in the lumen through the feed-tube, as by means of a piston.

FIG. 12 schematically illustrates a camera 402, or other device, attached to a piston 435 advancing inside the flexible sleeve 10. According to another embodiment, piston 435 is not attached to the camera but is used merely to propel the same.

Piston 435 is propelled by the pressure of the fluid 439 flowing within the flexible sleeve 10.

The flexible sleeve 10 part on the left side of piston 435 is shown deflated because the pressure inside this part of the flexible sleeve 10 is lower than that on the right side of piston 435.

The extent of this deflation can be partial, rather than full.

FIG. 12 shows the flexible sleeve 10 as fully unpacked (unfolded) on both sides of piston 435.

Another option is that piston 435 advances in the process of unpacking (unfolding) of the flexible sleeve 10.

According to another embodiment, piston 435 can be attached to the packed portion 117 of the flexible sleeve 10. Piston 435 can be of various shapes, materials, textures and degrees of pliancy.

According to another embodiment, piston 435 together with object 402 (e.g., a camera) can be introduced while the flexible sleeve 10 is not fully extended. Thus, the same advances as the flexible sleeve 10 is extended and advances.

According to another embodiment of the present invention, the object 403 (e.g., camera) and the piston 435 are introduced into the flexible sleeve 10 after the same has fully extended.

Reference is now made to FIG. 13. As piston 435 advances leftwards along and inside of the flexible sleeve 10, piston 435 eventually reaches the leftmost end of the same.

Accordingly, FIG. 13 shows piston 435 at the leftmost end of the flexible sleeve 10. At this end, the advance of piston 435 is stopped by a pre-positioned obstacle. An example of the pre-positioned obstacle in FIG. 13 is a narrowing in the cross sectional area of the flexible sleeve 10.

The obstacle maintains piston 435 at a position appropriate for subsequent functioning of camera 402, such as turning camera 402 on for taking images of space around the leftmost end of the flexible sleeve 10. Camera 402 attached to piston 435 is shown to face an opening, or a hole, in the flexible sleeve 10 so that the field of view 409 of camera 402 is unobstructed by the same.

Alternatively, the piston 435 is not coupled to object 402 and is used merely for propelling the same through the flexible sleeve 10.

The inspection of the colon wall is performed by taking still or video pictures (images) using camera 402. The image can be transmitted either wirelessly or by wire to a device for display or recording outside the body of the patient. Visual inspection may be performed while withdrawing the flexible sleeve 10, i.e. in real time.

Another option is to perform visual inspection of a recorded image, i.e., the image recorded during the withdrawal of the flexible sleeve 10 from the colon. The withdrawal of the same can be done by either manual or automated pulling of the tube by its proximal part (i.e., the part located outside of the body of the patient).

During its withdrawal from the colon, the flexible sleeve 10 is preferably kept under pressure by fluid 439 within the same, at a level comparable to or lower than the pressure during its advance into the colon.

Referring further to FIG. 13, in order to maintain the walls of the colon at a desired distance from camera 402, a toroidal balloon similar to balloons 405 and 408 in FIG. 10 (not shown in FIG. 13) can be inflated around the flexible sleeve 10 near the tube's leftmost end, where camera 402 is located.

The toroidal balloon can be attached to the outside surface of the flexible sleeve 10.

Another option is to attach the toroidal balloon to piston 435.

In either option, the inflation of such a balloon can be achieved upon piston 435 blocking the fluid exit at the leftmost end of the flexible sleeve 10, as shown in FIG. 13.

This blockage leads to the fluid pressure mounting inside the leftmost end of the flexible sleeve 10. This raises the pressure differential between the inside and the outside of the flexible sleeve 10.

The pressure differential inflates the toroidal balloon around the flexible sleeve 10, on the outside of the tube.

Another option is to inflate the toroidal balloon as part of the flexible sleeve 10, similarly to how balloon 408 is shown in FIG. 10. Optionally, the fluid can be allowed to slowly leak from the flexible sleeve 10 into the space between camera 402 and the colon wall for maintaining the distance between the wall of the colon and camera 402.

Thus, it is one object of the present invention to provide an endoscopic apparatus reversibly insertable into a curved lumen of a patient, comprising:

a. a flexible sleeve characterized by a proximal end and a distal end; the distal end of the flexible sleeve comprising:
  i. a flexible folded sleeve part comprising at least a portion of the flexible sleeve in a compact and folded arrangement, such that a compact and folded sleeve portion is enclosed within the folded sleeve part; the compact and folded sleeve portion is adapted to unfold and evert at least a portion of the compact and folded sleeve portion, as the same is advanced within the curved lumen of the patient; the folded sleeve part is characterized by a predetermined length $L_{fold}$;
  ii. an unfolded sleeve portion in communication with the compact folded sleeve part; the unfolded sleeve portion characterized by a length $L_{unfold}$; $L_{unfold}$ increases as at least a portion of the compact and folded sleeve portion unfolds and everts;
    wherein the compact and folded sleeve portion is enclosed and within the folded sleeve part such that a single topologically cylindrical sleeve is provided;

further wherein the enclosing of the compact and folded sleeve portion within the folded sleeve part is provided such that the flexible folded sleeve part advances with the curved lumen when at least a portion of the compact and folded sleeve portion unfolds and everts; further wherein the eversion is provided so as to increase the unfolded sleeve portion length $L_{unfold}$ and such that the flexible folded sleeve part self-navigates within the curved lumen.

It is another object of the present invention to provide the endoscopic apparatus as defined above, wherein the predetermined length $L_{fold}$ remains substantially the same when fluid is introduced into the folded sleeve part so as to evert and unfold at least a portion of the compact folded portion as the same advances within the curved lumen, such that longitudinal shearing forces between (a) at least one selected from a group consisting of (i) the folded sleeve part, (ii) the unfolded sleeve portion, and (iii) any combination thereof; and (b) the curved lumen is mitigated so as to enable advancement of the folded sleeve part within the curved lumen.

It is another object of the present invention to provide the endoscopic apparatus as defined above, wherein at least one of the following is being held true:
 a. the predetermined length $L_{fold}$ remains substantially the same when fluid is introduced into the flexible folded sleeve part casing and the compact and folded sleeve portion unfolds and everts;
 b. the predetermined length $L_{unfold}$ increases as at least a portion of the compact and folded sleeve portion unfolds and everts,
 such that longitudinal shearing forces between (a) at least one selected from a group consisting of (i) the folded sleeve casing, (ii) the unfolded sleeve portion, and (iii) any combination thereof; and (b) the curved lumen is mitigated.

It is another object of the present invention to provide the endoscopic apparatus as defined above, wherein the unfolding of at least a portion of the compact and folded sleeve portion is characterized by an unfolding function Y calculated as the ratio $L_{unfold}/L_{fold}$ as a function of time t, Y(t) represented by at least 2 regions:
 a. at least one first region $0<t<x1$; in which Y(t) substantially equals 1;
 b. at least one second region $t>x1$; in which Y(t) is greater than 1.

It is another object of the present invention to provide the endoscopic apparatus as defined above, additionally comprising fluid input means, in fluid communication with the folded sleeve part, adapted to introduce fluid into the same so as to unfold at least part of the compact folded portion.

It is another object of the present invention to provide the endoscopic apparatus as defined above, wherein the fluid is selected from a group consisting of gas, liquid and any combination thereof.

It is another object of the present invention to provide the endoscopic apparatus as defined above, additionally comprising an inflating tube, coupled to the unfolded sleeve portion, adapted to inflate at least a portion of the compact and folded sleeve portion.

It is another object of the present invention to provide the endoscopic apparatus as defined above, wherein the tube is adapted to deflate the flexible sleeve for withdrawal of the same from the curved lumen.

It is another object of the present invention to provide the endoscopic apparatus as defined above, wherein the curved lumen is the gastrointestinal tract.

It is another object of the present invention to provide the endoscopic apparatus as defined above, wherein the apparatus is adapted for cleansing a colon of a patient.

It is another object of the present invention to provide the endoscopic apparatus as defined above, wherein the endoscopic apparatus is adapted to enable inspection of the curved lumen.

It is another object of the present invention to provide the endoscopic apparatus as defined above, wherein the compact and folded arrangement of the compact and folded sleeve portion is selected from a group consisting of telescopic arrangement, accordion arrangement, spiral-like rolled arrangement, zigzag arrangement and any combination thereof.

It is another object of the present invention to provide the endoscopic apparatus as defined above, wherein the cross section of the flexible folded sleeve part is a constant cross section along the length of the same.

It is another object of the present invention to provide the endoscopic apparatus as defined above, wherein the cross section of the flexible folded sleeve part is a varied cross section along the length of the same.

It is another object of the present invention to provide the endoscopic apparatus as defined above, wherein at least a part of the flexible folded sleeve part has a cross-section that is quasi-periodically variable along the length of the flexible sleeve.

It is another object of the present invention to provide the endoscopic apparatus as defined above, wherein at least a part of the cross section of the flexible folded sleeve part is a sausage-chain-like cross section, a bead-string-like cross section and any combination thereof.

It is another object of the present invention to provide the endoscopic apparatus as defined above, wherein the diameter of the flexible sleeve does not alter when the same is inflated.

It is another object of the present invention to provide the endoscopic apparatus as defined above, wherein the flexible sleeve additionally comprises at least one aperture.

It is another object of the present invention to provide the endoscopic apparatus as defined above, wherein the flexible sleeve is adapted for cleansing the lumen, such that cleansing fluids exit and outflow from the aperture.

It is another object of the present invention to provide the endoscopic apparatus as defined above, additionally comprising a removable cap adapted to ease the insertion of the flexible sleeve into the lumen.

It is another object of the present invention to provide the endoscopic apparatus as defined above, wherein the removable cap is filled with water.

It is another object of the present invention to provide the endoscopic apparatus as defined above, wherein the removable cap is made of a material that would melt, soften, dissolve and any combination thereof upon being inserted into the lumen.

It is another object of the present invention to provide the endoscopic apparatus as defined above, wherein the removable cap comprises several segments, each of which is small enough to be pulled back through the flexible sleeve with a flow of liquid.

It is another object of the present invention to provide the endoscopic apparatus as defined above, wherein the flexible sleeve is made of materials selected from a group consisting of polyethylene (preferably low density polyethylene), polypropylene, polyurethane and any combination thereof.

It is another object of the present invention to provide the endoscopic apparatus as defined above, wherein the flexible sleeve is designed and constructed so as to enable the insertion of an endoscope into the same.

It is another object of the present invention to provide the endoscopic apparatus as defined above, wherein the flexible sleeve is designed and constructed so as to enable the insertion of an object into the same.

It is another object of the present invention to provide the endoscopic apparatus as defined above, wherein the object is selected from a group consisting of a camera, a detachable capsule, a source of radiation, a source of light, a source of X-rays, a source of positrons, a source of other radioactivity, and any combination thereof.

It is another object of the present invention to provide the endoscopic apparatus as defined above, wherein the object is coupled directly to the flexible sleeve.

It is another object of the present invention to provide the endoscopic apparatus as defined above, wherein the object is introduced into the flexible sleeve after the same has been fully extended within the lumen.

It is another object of the present invention to provide the endoscopic apparatus as defined above, wherein the object is introduced into the flexible sleeve while the same is not fully extended within the lumen, such that the object advances with the flexible sleeve.

It is another object of the present invention to provide the endoscopic apparatus as defined above, wherein the flexible sleeve is characterized by at least one wider section of the same.

It is another object of the present invention to provide the endoscopic apparatus as defined above, wherein the at least one wider section is adapted to spread the wall of the lumen so as to enable visual examination of the same.

It is another object of the present invention to provide the endoscopic apparatus as defined above, wherein a plurality of cameras are coupled to at least one location of the flexible sleeve.

It is another object of the present invention to provide the endoscopic apparatus as defined above, wherein a plurality of cameras are introduced into the flexible sleeve.

It is another object of the present invention to provide the endoscopic apparatus as defined above, wherein at least one contrast agent adapted for medical imaging of the lumen is introduced into the flexible sleeve.

It is another object of the present invention to provide the endoscopic apparatus as defined above, wherein the at least one contrast agent is introduced once the flexible sleeve is fully extended.

It is another object of the present invention to provide the endoscopic apparatus as defined above, wherein the at least one contrast agent is selected from a group consisting of barium sulfate, water soluble contrast agents and any combination thereof.

It is another object of the present invention to provide the endoscopic apparatus as defined above, wherein at least one medication is introduced through the flexible sleeve into said lumen.

It is another object of the present invention to provide the endoscopic apparatus as defined above, wherein the flexible sleeve is adapted to massage at least a part of the wall of the lumen.

It is another object of the present invention to provide the endoscopic apparatus as defined above, wherein the flexible sleeve conforms to the walls of the lumen so as to massage the same.

It is another object of the present invention to provide the endoscopic apparatus as defined above, wherein at least a portion of the flexible sleeve is characterized by a narrower cross sectional area.

It is another object of the present invention to provide the endoscopic apparatus as defined above, wherein at least one selected from a group consisting of the folded sleeve portion, the unfolded sleeve portion and any combination thereof additionally comprises at least one element selected from a group consisting of at least one camera adapted to provide either 2D or 3D real time images, an ultrasound sensor, a source of ultrasound, a radiation sensor, a source of radiation and any combination thereof.

It is another object of the present invention to provide the endoscopic apparatus as defined above, wherein a piston is introduced into the flexible sleeve and propelled inside the same by pressure of a fluid being pumped into the flexible sleeve.

It is another object of the present invention to provide the endoscopic apparatus as defined above, wherein the piston is coupled to an object.

It is another object of the present invention to provide the endoscopic apparatus as defined above, wherein the piston is in communication with an object.

It is another object of the present invention to provide the endoscopic apparatus as defined above, wherein the object is selected from a group consisting of at least one camera adapted to provide either 2D or 3D real time images, an ultrasound sensor, a source of ultrasound, a radiation sensor, a source of radiation and any combination thereof.

It is another object of the present invention to provide the endoscopic apparatus as defined above, wherein the object is a camera; further wherein the camera is adapted to take images while the flexible sleeve is being withdrawn from the lumen; the image is being used for visual inspection of space around the camera upon recording the image, in real time and any combination thereof.

It is another object of the present invention to provide the endoscopic apparatus as defined above, wherein the flexible sleeve comprises at least one opening through which the camera has a view unobstructed by the flexible sleeve.

It is another object of the present invention to provide the endoscopic apparatus as defined above, wherein the advance of the piston is stopped by a prepositioned obstacle at a position appropriate for subsequent functioning of the piston.

It is another object of the present invention to provide the endoscopic apparatus as defined above, additionally comprising a drainage channel adapted for insertion into a lumen, the flexible sleeve is disposed inside and extending through the drainage channel and the lumen, whereby washing liquid is drained out of the lumen through the drainage channel.

It is another object of the present invention to provide the endoscopic apparatus as defined above, additionally comprising at least one inflatable balloon coupled to the drainage channel; the balloon is inflated inside the lumen; the inflated balloon together with the drainage channel maintains the drainage channel in position and prevents any unwanted movements.

It is another object of the present invention to provide the endoscopic apparatus as defined above, additionally comprising a delivery tube characterized by a distal end and a proximal end interconnected to one another by a hollow bore, said delivery tube fluidly connectable at its distal end to said proximal end of said flexible sleeve.

It is another object of the present invention to provide the endoscopic apparatus as defined above wherein said delivery tube is substantially cylindrical.

It is another object of the present invention to provide the endoscopic apparatus as defined above, wherein said delivery tube is removably attachable to said proximal end of flexible sleeve.

It is another object of the present invention to provide the endoscopic apparatus as defined above, additionally comprising an attachment means, located at said distal end of said delivery tube; adapted to provide attachment between said distal end of said delivery tube and said proximal end of said flexible sleeve.

It is another object of the present invention to provide the endoscopic apparatus as defined above, wherein said attachment means is selected from a group consisting of: an elastic band, an elastic tie, a ribbon, a tape, a catch, a clip and any combination thereof.

It is another object of the present invention to provide the endoscopic apparatus as defined above, additionally comprising a flange located at said distal end of said delivery tube, said flange is unitary with said distal end of said delivery tube, said distal end wider than said proximal end.

It is another object of the present invention to provide the endoscopic apparatus as defined above, wherein the shape of said flange is selected from a group consisting of substantially conical, substantially spherical, substantially ellipsoidal, substantially ovoid, substantially hyperboloid, and any combination thereof.

It is another object of the present invention to provide the endoscopic apparatus as defined above, wherein the diameter of said flange is in the range of approximately 2 times the diameter of said delivery tube to approximately 5 times said diameter of said delivery tube.

It is another object of the present invention to provide the endoscopic apparatus as defined above, wherein said hollow bore is adapted to deliver at least one fluid to unfold and evert at least a portion of said compact and folded sleeve portion.

It is another object of the present invention to provide the endoscopic apparatus as defined above, wherein said fluid is selected from a group consisting of a liquid, a gas and any combination thereof.

It is another object of the present invention to provide the endoscopic apparatus as defined above, wherein said liquid comprises members of a group consisting of saline, water, washing liquid, sodium phosphate, baking soda, barium compounds, mineral oil, glycerin, laxatives, medicaments, and any combination thereof.

It is another object of the present invention to provide the endoscopic apparatus as defined above, wherein said gas is selected from a group consisting of air, nitrogen, oxygen, CO2, xenon and any combination thereof.

It is another object of the present invention to provide a method of extending a tube within a curved lumen; comprising steps of:
  a. obtaining a flexible sleeve, comprising:
    i. a flexible folded sleeve part comprising at least a portion of the flexible sleeve in a compact and folded arrangement, such that a compact and folded sleeve portion is enclosed within the folded sleeve part; the compact and folded sleeve portion is adapted to unfold and evert at least a portion of the compact and folded sleeve portion, as the same is advanced within the curved lumen of the patient; the folded sleeve part is characterized by a predetermined length $L_{fold}$;
    ii. an unfolded sleeve portion in communication with the compact folded sleeve part; the unfolded sleeve portion characterized by a length $L_{unfold}$; $L_{unfold}$ increases as at least a portion of the compact and folded sleeve portion unfolds and everts;
  wherein the compact and folded sleeve portion is enclosed and within the folded sleeve part such that a single topologically cylindrical sleeve is provided;
  further wherein the enclosing of the compact and folded sleeve portion within the folded sleeve part is provided such that the flexible folded sleeve part advances with the curved lumen when at least a portion of the compact and folded sleeve portion unfolds and everts; further wherein the eversion is provided so as to increase the unfolded sleeve portion length $L_{unfold}$ and such that the flexible folded sleeve part self-navigates within the curved lumen
  b. inserting the flexible sleeve into the lumen;
  c. introducing a fluid into said flexible folded sleeve part, thereby unfolding and everting said at least a portion of said compact and folded sleeve portion;
  d. extending said flexible sleeve within said curved lumen.

It is another object of the present invention to provide the method as defined above, wherein said predetermined length $L_{fold}$ remains substantially the same when fluid is introduced into the folded sleeve part so as to evert and unfold at least a portion of the compact folded portion as the same advances within the curved lumen, such that longitudinal shearing forces between (a) at least one selected from a group consisting of (i) the folded sleeve part, (ii) the unfolded sleeve portion, and (iii) any combination thereof; and (b) the curved lumen is mitigated so as to enable advancement of the folded sleeve part within the curved lumen.

It is another object of the present invention to provide the method as defined above, wherein at least one of the following is being held true:
  a. the predetermined length $L_{fold}$ remains substantially the same when fluid is introduced into the flexible folded sleeve part casing and the compact and folded sleeve portion unfolds and everts;
  b. the predetermined length $L_{unfold}$ increases as at least a portion of the compact and folded sleeve portion unfolds and everts,
  such that longitudinal shearing forces between (a) at least one selected from a group consisting of (i) the folded sleeve casing, (ii) the unfolded sleeve portion, and (iii) any combination thereof and (b) the curved lumen is mitigated.

It is another object of the present invention to provide the method as defined above, wherein the unfolding of at least a portion of the compact and folded sleeve portion is characterized by an unfolding function Y calculated as the ratio $L_{unfold}/L_{fold}$ as a function of time t, Y(t) represented by at least 2 regions:
  a. at least one first region 0<t<x1; in which Y(t) substantially equals 1;
  b. at least one second region t>x1; in which Y(t) is greater than 1.

It is another object of the present invention to provide the method as defined above, additionally comprising a step of providing the endoscopic apparatus with fluid input means, in fluid communication with the folded sleeve part, adapted to introduce fluid into the same so as to unfold at least part of the compact folded portion.

It is another object of the present invention to provide the method as defined above, wherein the fluid is selected from a group consisting of gas, liquid and any combination thereof.

It is another object of the present invention to provide the method as defined above, additionally comprising a step of providing the endoscopic apparatus with an inflating tube coupled to the unfolded sleeve portion, adapted to inflate at least a portion of the compact and folded sleeve portion.

It is another object of the present invention to provide the method as defined above, wherein the tube is adapted to deflate the flexible sleeve for withdrawal of the same from the curved lumen.

It is another object of the present invention to provide the method as defined above, wherein the curved lumen is the gastrointestinal tract and the colon of a patient.

It is another object of the present invention to provide the method as defined above, wherein the apparatus is adapted for cleansing a colon of a patient.

It is another object of the present invention to provide the method as defined above, wherein the endoscopic apparatus is adapted to enable inspection of the curved lumen.

It is another object of the present invention to provide the method as defined above, wherein said compact and folded arrangement of said compact and folded sleeve portion is selected from a group consisting of telescopic arrangement, accordion arrangement, zigzag arrangement, spiral-like rolled arrangement and any combination thereof.

It is another object of the present invention to provide the method as defined above, wherein the cross section of the flexible folded sleeve part is a constant cross section along the length of the same.

It is another object of the present invention to provide the method as defined above, wherein the cross section of the flexible folded sleeve part is a varied cross section along the length of the same.

It is another object of the present invention to provide the method as defined above, wherein at least a part of the flexible folded sleeve part has a cross-section that is quasi-periodically variable along the length of the flexible sleeve.

It is another object of the present invention to provide the method as defined above, wherein at least a part of the cross section of the flexible folded sleeve part is a sausage-chain-like cross section, a bead-string-like cross section and any combination thereof.

It is another object of the present invention to provide the method as defined above, additionally comprising a step of setting the diameter of the flexible sleeve such that the diameter does not alter when the flexible sleeve is inflated.

It is another object of the present invention to provide the method as defined above, additionally comprising a step of providing the flexible sleeve with at least one aperture.

It is another object of the present invention to provide the method as defined above, wherein the flexible sleeve is adapted for cleansing thelumen, such that cleansing fluids exits and outflow from the aperture.

It is another object of the present invention to provide the method as defined above, additionally comprising a step of providing theflexible sleeve with a removable cap adapted to ease insertion of the flexible sleeve into the lumen.

It is another object of the present invention to provide the method as defined above, wherein the removable cap is filled with water.

It is another object of the present invention to provide the method as defined above, wherein the removable cap is made of a material that would melt, soften, dissolve and any combination thereof upon being inserted into said lumen.

It is another object of the present invention to provide the method as defined above, wherein the removable cap comprises several segments, each of which is small enough to be pulled back through the flexible sleeve with a flow of liquid.

It is another object of the present invention to provide the method as defined above, wherein the flexible sleeve is made of materials selected from a group consisting of polyethylene (preferably low density polyethylene), polypropylene, polyurethane and any combination thereof.

It is another object of the present invention to provide the method as defined above, additionally comprising a step of designing and constructing the flexible sleeve so as to enable the insertion of an endoscope into the same.

It is another object of the present invention to provide the method as defined above, additionally comprising a step of designing and constructing the flexible sleeve so as to enable the insertion of an object into the same.

It is another object of the present invention to provide the method as defined above, wherein said object is selected from a group consisting of camera, a detachable capsule, a source of radiation, a source of light, a source of X-rays, a source of positrons, a source of other radioactivity, and any combination thereof.

It is another object of the present invention to provide the method as defined above, wherein the object is coupled directly to the flexible sleeve.

It is another object of the present invention to provide the method as defined above, wherein the object is introduced into the flexible sleeve after the same has been fully extended within the lumen.

It is another object of the present invention to provide the method as defined above, wherein the object is introduced into the flexible sleeve while the same is not fully extended within the lumen, such that the object advances with the flexible sleeve.

It is another object of the present invention to provide the method as defined above, wherein the flexible sleeve is characterized by at least one wider section of the same.

It is another object of the present invention to provide the method as defined above, wherein the at least one wider section is adapted to spread the wall of the lumen so as to enable visual examination of the same.

It is another object of the present invention to provide the method as defined above, additionally comprising a step of coupling a plurality of cameras to at least one location of the flexible sleeve.

It is another object of the present invention to provide the method as defined above, additionally comprising a step of introducing a plurality of cameras into the flexible sleeve.

It is another object of the present invention to provide the method as defined above, additionally comprising a step of introducing at least one contrast agent adapted for medical imaging of the lumen into the flexible sleeve.

It is another object of the present invention to provide the method as defined above, wherein the at least one contrast agent is introduced once the flexible sleeve is fully extended.

It is another object of the present invention to provide the method as defined above, wherein the at least one contrast agent is selected from a group consisting of barium sulfate, water soluble contrast agents and any combination thereof.

It is another object of the present invention to provide the method as defined above, additionally comprising a step of introducing at least one medication through the flexible sleeve into the lumen.

It is another object of the present invention to provide the method as defined above, additionally comprising a step of massaging at least a part of the wall of the lumen.

It is another object of the present invention to provide the method as defined above, wherein the flexible sleeve conforms to the walls of the lumen so as to massage the same.

It is another object of the present invention to provide the method as defined above, additionally comprising a step of providing the flexible sleeve with at least a portion of the same being characterized by a narrower cross sectional area.

It is another object of the present invention to provide the method as defined above, wherein at least one selected from a group consisting of the folded sleeve portion, the unfolded sleeve portion and any combination thereof additionally comprises at least one element selected from a group consisting of at least one camera adapted to provide either 2D or 3D real time images, an ultrasound sensor, a source of ultrasound, a radiation sensor, a source of radiation and any combination thereof.

It is another object of the present invention to provide the method as defined above, additionally comprising a step of introducing a piston into the flexible sleeve and propelling the same inside the flexible sleeve by pressure of a fluid being pumped into the flexible sleeve.

It is another object of the present invention to provide the method as defined above, wherein the piston is coupled to an object.

It is another object of the present invention to provide the method as defined above, wherein the piston is in communication with an object.

It is another object of the present invention to provide the method as defined above, wherein the object is selected from a group consisting of at least one camera adapted to provide either 2D or 3D real time images, an ultrasound sensor, a source of ultrasound, a radiation sensor, a source of radiation and any combination thereof.

It is another object of the present invention to provide the method as defined above, wherein the object is a camera; further wherein the camera is adapted to take images while the flexible sleeve is being withdrawn from the lumen; the image is being used for visual inspection of space around the camera upon recording the image, in real time and any combination thereof.

It is another object of the present invention to provide the method as defined above, wherein the flexible sleeve comprises at least one opening through which the camera has a view unobstructed by the flexible sleeve.

It is another object of the present invention to provide the method as defined above, wherein the advance of the piston is stopped by a prepositioned obstacle at a position appropriate for subsequent functioning of the piston.

It is another object of the present invention to provide the method as defined above, additionally comprising a drainage channel adapted for insertion into a lumen, the flexible sleeve disposed inside and extending through the drainage channel and the lumen, whereby washing liquid is drained out of the lumen through the drainage channel.

It is another object of the present invention to provide the method as defined above, additionally comprising at least one inflatable balloon coupled to the drainage channel; the balloon inflated inside the lumen; the inflated balloon together with the drainage channel maintaining the drainage channel in position and preventing any unwanted movements. It is another object of the present invention to provide the method as defined above, additionally comprising a delivery tube characterized by a distal end and a proximal end interconnected to one another by a hollow bore, said delivery tube fluidly connectable at its distal end to said proximal end of said flexible sleeve.

It is another object of the present invention to provide the method as defined above, additionally comprising a step of selecting said delivery tube to be substantially cylindrical.

It is another object of the present invention to provide the method as defined above, additionally comprising a step of providing said delivery tube removably attachable to said proximal end of flexible sleeve.

It is another object of the present invention to provide the method as defined above, additionally comprising an attachment means, located at said distal end of said delivery tube; adapted to provide attachment between said distal end of said delivery tube and said proximal end of said flexible sleeve.

It is another object of the present invention to provide the method as defined above, additionally comprising a step of selecting said attachment means from a group consisting of: an elastic band, an elastic tie, a ribbon, a tape, a catch, a clip and any combination thereof.

It is another object of the present invention to provide the method as defined above, additionally comprising a step of providing a flange located at said distal end of said delivery tube, said flange is unitary with said distal end of said delivery tube, said distal end wider than said proximal end.

It is another object of the present invention to provide the method as defined above, additionally comprising a step of selecting the shape of said flange from a group consisting of substantially conical, substantially spherical, substantially ellipsoidal, substantially ovoid, substantially hyperboloid, and any combination thereof.

It is another object of the present invention to provide the method as defined above, additionally comprising a step of selecting the diameter of said flange to be in the range of approximately 2 times the diameter of said delivery tube to approximately 5 times said diameter of said delivery tube.

It is another object of the present invention to provide the method as defined above, additionally comprising a step of adapting said hollow bore to deliver at least one fluid to unfold and evert at least a portion of said compact and folded sleeve portion.

It is another object of the present invention to provide the method as defined above, additionally comprising a step of selecting said fluid from a group consisting of a liquid, a gas and any combination thereof.

It is another object of the present invention to provide the method as defined above, additionally comprising a step of comprising said liquid of members of a group consisting of saline, water, washing liquid, sodium phosphate, baking soda, barium compounds, mineral oil, glycerin, laxatives, medicaments, and any combination thereof.

It is another object of the present invention to provide the method as defined above, additionally comprising a step of selecting said gas from a group consisting of air, nitrogen, oxygen, CO2, xenon and any combination thereof.

The foregoing description of a preferred embodiment and best mode of the invention known to the applicant at the time of filing the application has been presented for the purposes of illustration and description. It is not intended to be exhaustive or to limit the invention to the precise form disclosed, and obviously many modifications and variations are possible in the light of the above teaching. The embodiment was chosen and described in order to best explain the principles of the invention and its practical application to thereby enable others skilled in the art to best utilize the invention in various embodiments and with various modifications as are suited to the particular use contemplated.

The references cited herein teach many principles that are applicable to the present invention. Therefore the full contents of these publications are incorporated by reference herein where appropriate for teachings of additional or alternative details, features and/or technical background. It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. An endoscopic apparatus reversibly insertable into a curved lumen of a patient, said apparatus comprising:
   a flexible sleeve having a length, a proximal end, a distal end, and a longitudinal axis;
   said distal end of said flexible sleeve comprising:
      a folded sleeve portion having a length $L_{fold}$;
      a compact folded portion enclosed within said folded sleeve portion such that a single topologically cylindrical sleeve is provided; said compact folded portion comprising a spiral structure in which at least a part of said flexible sleeve portion has been rolled from said distal end about an axis of rotation and rotated so that said axis of rotation is parallel to said longitudinal axis, such that when said sleeve is inflated by fluid, said compact folded portion partially unfolds and everts radially from said folded sleeve portion; and
      an unfolded sleeve portion connecting said compact folded portion to said folded sleeve portion; said unfolded sleeve portion having a length $L_{unfold}$ that increases as at least a portion of said compact folded portion unfolds and everts when said sleeve is inflated by fluid;
   wherein:
   when in use, said folded sleeve portion extends distally when at least a portion of said compact folded portion unfolds and everts;
   said eversion is provided so as to increase said unfolded sleeve portion length $L_{unfold}$ and such that when in use said folded sleeve portion self-navigates within said curved lumen when said sleeve is inflated by fluid; and
   said unfolded sleeve portion substantially stays stationary when said sleeve is inflated by fluid.

2. The endoscopic apparatus according to claim 1, wherein said length $L_{fold}$ remains substantially the same when fluid is introduced into said folded sleeve part so as to evert and unfold at least a portion of said compact folded portion as said compact folded portion advances within said curved lumen, such that longitudinal shearing forces between (a) at least one selected from a group consisting of (i) said folded sleeve portion, (ii) said unfolded sleeve portion, and (iii) any combination thereof; and (b) said curved lumen is mitigated so as to enable advancement of said folded sleeve part within said curved lumen.

3. The endoscopic apparatus according to claim 1, wherein at least one of the following is true:
   said length $L_{fold}$ remains substantially the same when fluid is introduced into said folded sleeve portion and said compact folded portion unfolds and everts;
   said length $L_{unfold}$ increases as at least a portion of compact folded portion unfolds and everts, such that longitudinal shearing forces between (a) at least one selected from a group consisting of (i) said folded sleeve, (ii) said unfolded sleeve portion, and (iii) any combination thereof; and (b) said curved lumen is mitigated.

4. The endoscopic apparatus according to claim 1, wherein said unfolding of at least a portion of said compact folded portion is configured to have an unfolding function Y calculated as a ratio $L_{unfold}/L_{fold}$ as a function of time t, Y(t) represented by at least 2 regions:
   at least one first region 0<t<x1; in which said Y(t) substantially equals 1;
   at least one second region t>x1; in which said Y(t) is greater than 1.

5. The endoscopic apparatus according to claim 1, additionally comprising fluid input means, in fluid communication with said folded sleeve portion, for introducing fluid into said folded sleeve portion so as to unfold at least part of said compact folded portion; further wherein said fluid is selected from a group consisting of gas, liquid and any combination thereof.

6. The endoscopic apparatus according to claim 1, additionally comprising an inflating tube, coupled to said unfolded sleeve portion, adapted to inflate at least a portion of said compact folded portion; further wherein said tube is adapted to deflate said flexible sleeve for withdrawal of the same from said curved lumen.

7. The endoscopic apparatus according to claim 1, wherein said apparatus is adapted for cleansing a colon of a patient, such that said curved lumen is the gastrointestinal tract.

8. The endoscopic apparatus according to claim 1, wherein at least one of the following is true
   said folded sleeve portion has a constant cross section along a length of the folded sleeve portion;
   said folded sleeve portion has a cross section that is variable along a length of the folded sleeve portion;
   at least a part of said folded sleeve portion has a cross-section that is quasi-periodically variable along the length of folded sleeve portion;
   at least a part of said folded sleeve portion has a shape selected from the group consisting of a sausage-chain, a bead-string and any combination thereof; and any combination thereof.

9. The endoscopic apparatus according to claim 1, wherein said flexible sleeve additionally comprises at least one aperture configured to allow exit and outflow of cleansing fluids.

10. The endoscopic apparatus according to claim 1, additionally comprising a removable cap adapted to ease the insertion of said flexible sleeve into said lumen; further wherein said removable cap is filled with water, made of a material that will melt, soften, dissolve or any combination thereof upon being inserted into said lumen and comprises several segments, each of which is small enough to be pulled back through said flexible sleeve with a flow of liquid.

11. The endoscopic apparatus according to claim 1, wherein at least one of the following is true:
   said flexible sleeve is made of materials selected from the group consisting of polyethylene, low density polyethylene, polypropylene, polyurethane and any combination thereof; and
   said flexible sleeve is designed and constructed so as to enable the insertion of an object selected from the group consisting of an endoscope, a camera, a detachable capsule, a source of radiation, a source of light, a source of X-rays, a source of positrons, a source of other radioactivity, and any combination thereof into said flexible sleeve.

12. The endoscopic apparatus according to claim 11, wherein at least one of the following is true:
said object is coupled directly to said flexible sleeve;
said object is introduced into said flexible sleeve after the same has been fully extended within said lumen; and
said object is configured to be introduced into said flexible sleeve while the flexible sleeve is not fully extended within said lumen, such that said object advances with said flexible sleeve.

13. The endoscopic apparatus according to claim 1, wherein at least one of the following is true:
said flexible sleeve has at least one wider section adapted to spread the wall of said lumen so as to enable visual examination of the said lumen;
a plurality of cameras are coupled to at least one location of said flexible sleeve;
a plurality of cameras are interdisposed within said flexible sleeve;
said flexible sleeve is configured to admit at least one contrast agent adapted for medical imaging of said lumen, said at least one contrast agent being selected from the group consisting of barium sulfate, water soluble contrast agents and any combination thereof;
said flexible sleeve is configured to introduce at least one medication into said lumen; and
said flexible sleeve is adapted to massage at least a part of the wall of said lumen.

14. The endoscopic apparatus according claim 1, wherein at least one selected from a group consisting of said folded sleeve portion, said unfolded sleeve portion and any combination thereof additionally comprises at least one element selected from the group consisting of at least one camera adapted to provide either 2D or 3D real time images, an ultrasound sensor, a source of ultrasound, a radiation sensor, a source of radiation and any combination thereof.

15. The endoscopic apparatus according to claim 1, comprising a piston disposed within said flexible sleeve and configured to be propelled inside said flexible sleeve by pressure of a fluid being pumped thereinto.

16. The endoscopic apparatus according to claim 15, wherein at least one of the following is true:
said piston is coupled to an object; and
said piston is in communication with an object.

17. The endoscopic apparatus according to claim 16, wherein at least one of the following is true:
said object is selected from the group consisting of at least one endoscope, a camera adapted to provide either 2D or 3D real time images, an ultrasound sensor, a source of ultrasound, a radiation sensor, a source of radiation and any combination thereof;
said object is a camera adapted to take images for visual inspection of space around said camera either upon recording said image or in real time while said flexible sleeve is being withdrawn from said lumen, and said flexible sleeve comprises at least one opening through which said camera has a view unobstructed by said flexible sleeve.

18. The endoscopic apparatus according to claim 1, additionally comprising:
a drainage channel adapted for insertion into said lumen and configured to drain washing fluid out of said lumen through said drainage channel, said flexible sleeve being disposed inside and extending through said drainage channel and said lumen; and
optionally, at least one inflatable balloon inflated inside said lumen and coupled to said drainage channel; wherein said inflated balloon together with said drainage channel are configured to maintain said drainage channel in position and prevent any unwanted movements.

19. The endoscopic apparatus according to claim 1, additionally comprising a delivery tube having a distal end and a proximal end interconnected to one another by a hollow bore, said delivery tube fluidly connectable at its distal end to said proximal end of said flexible sleeve; wherein said delivery tube is removably attachable to said proximal end of flexible sleeve.

20. The endoscopic apparatus according to claim 19, additionally comprising at said distal end of said delivery tube, an attachment means for attaching said distal end of said delivery tube to said proximal end of said flexible sleeve; said attachment means being selected from the group consisting of: an elastic band, an elastic tie, a ribbon, a tape, a catch, a clip and any combination thereof.

21. The endoscopic apparatus according to claim 20, additionally comprising a flange located at said distal end of said delivery tube, said flange is unitary with said distal end of said delivery tube, said distal end wider than said proximal end.

22. The endoscopic apparatus according to claim 21, wherein the shape of said flange is selected from the group consisting of substantially conical, substantially spherical, substantially ellipsoidal, substantially ovoid, substantially hyperboloid, and any combination thereof.

23. The endoscopic apparatus according to claim 22, wherein the diameter of said flange is in the range of approximately 2 times the diameter of said delivery tube to approximately 5 times said diameter of said delivery tube; further wherein said hollow bore is adapted to deliver at least one fluid to unfold and evert at least a portion of said compact folded portion.

24. The endoscopic apparatus according to claim 23, wherein said fluid is selected from the group consisting of:
a liquid selected from the group consisting of saline, water, washing liquid, sodium phosphate, baking soda solution, solutions of barium compounds, mineral oil, glycerin, laxatives, medicaments, and any combination thereof;
a gas being selected from the group consisting of air, nitrogen, oxygen, $CO_2$, xenon and any combination thereof; and
any combination thereof.

25. A method of extending a tube within a curved lumen, the method comprising steps of:
obtaining an apparatus comprising a flexible sleeve having a length, a proximal end, a distal end, and a longitudinal axis;
said distal end of said flexible sleeve comprising:
a folded sleeve portion having a length $L_{fold}$;
a compact folded portion enclosed within said folded sleeve portion such that a single topologically cylindrical sleeve is provided; said compact folded portion comprising a spiral structure in which at least a part of said flexible sleeve portion has been rolled from said distal end about an axis of rotation and rotated by 90° so that said axis of rotation is parallel to said longitudinal axis, such that when said sleeve is inflated by fluid, said compact folded portion partially unfolds and everts radially from said folded sleeve portion; and
an unfolded sleeve portion connecting said compact folded portion to said folded sleeve portion; said unfolded sleeve portion having a length $L_{unfold}$ that increases as at least a portion of said compact folded portion unfolds and everts when said sleeve is inflated by fluid;
  inserting said flexible sleeve into said lumen;
  introducing a fluid into said folded sleeve portion, thereby unfolding and everting said at least a portion of said compact folded portion; and
  extending said flexible sleeve within said curved lumen.

26. The method according to claim 25, wherein said length $L_{fold}$ remains substantially the same when fluid is introduced into said folded sleeve part so as to evert and unfold at least a portion of said compact folded portion as the same advances within said curved lumen, such that longitudinal shearing forces between (a) at least one selected from a group consisting of (i) said folded sleeve part, (ii) said unfolded sleeve portion, and (iii) any combination thereof; and (b) said curved lumen is mitigated so as to enable advancement of said folded sleeve part within said curved lumen.

27. The method according to claim 25 wherein at least one of the following is true:
  said length $L_{fold}$ remains substantially the same when fluid is introduced into said flexible folded sleeve part casing and said compact folded portion unfolds and everts;
  said length $L_{unfold}$ increases as at least a portion of compact folded portion unfolds and everts,
  such that longitudinal shearing forces between (a) at least one selected from a group consisting of (i) said folded sleeve casing, (ii) said unfolded sleeve portion, and (iii) any combination thereof; and (b) said curved lumen is mitigated.

28. The method according to claim 25, additionally comprising providing a delivery tube removably attachable to said proximal end of flexible sleeve, having a distal end and a proximal end interconnected to one another by a hollow bore, said delivery tube fluidly connectable at its distal end to said proximal end of said flexible sleeve.

* * * * *